(12) United States Patent
Gibbins et al.

(10) Patent No.: US 8,944,055 B2
(45) Date of Patent: Feb. 3, 2015

(54) INHALER

(75) Inventors: Graham Gibbins, Cambridge (GB); Ben Tyers, Lancashire (GB); Andreas Mark Meliniotis, Cambridge (GB)

(73) Assignee: Vectura Delivery Devices Limited, Chippenham (GB)

( * ) Notice: Subject to any disclaimer, the term of this patent is extended or adjusted under 35 U.S.C. 154(b) by 724 days.

(21) Appl. No.: 12/864,339

(22) PCT Filed: Jan. 22, 2009

(86) PCT No.: PCT/EP2009/050730
§ 371 (c)(1),
(2), (4) Date: Oct. 14, 2010

(87) PCT Pub. No.: WO2009/092768
PCT Pub. Date: Jul. 30, 2009

(65) Prior Publication Data
US 2011/0048420 A1 Mar. 3, 2011

(30) Foreign Application Priority Data

Jan. 24, 2008 (EP) ................................... 08100881

(51) Int. Cl.
A61M 15/00 (2006.01)
A61M 16/00 (2006.01)
A61M 11/00 (2006.01)
B05B 1/26 (2006.01)
(Continued)

(52) U.S. Cl.
CPC ....... *A61M 15/0045* (2013.01); *A61M 15/0021* (2014.02); *A61M 15/0025* (2014.02); *A61M 15/0033* (2014.02); *A61M 15/0036* (2014.02);
*A61M 15/0041* (2014.02); *A61M 15/0051* (2014.02); *A61M 2202/064* (2013.01)
USPC ............ 128/203.21; 128/200.14; 128/200.17; 128/205.21

(58) Field of Classification Search
CPC .................. A61M 2015/0051; A61M 15/0045
USPC ...................................................... 128/203.19
See application file for complete search history.

(56) References Cited

U.S. PATENT DOCUMENTS 7,171,965 B2 * 2/2007 Young et al. ............. 128/203.15
7,779,839 B2 * 8/2010 Pocock et al. ........... 128/203.21
(Continued)

FOREIGN PATENT DOCUMENTS

CN 1622838 A 6/2005
CN 1867369 A 11/2006
(Continued)

OTHER PUBLICATIONS

International Search Report issued in connection with International Patent Application No. PCT/EP2009/050730.
(Continued)

*Primary Examiner* — Oren Ginsberg
*Assistant Examiner* — Joshua Lee

(57) ABSTRACT

An inhaler is disclosed. It comprises a housing to receive a strip having a surface and a plurality of blister pockets depending from said surface. Each blister pocket contains a dose of medicament for inhalation by a user. The inhaler has a blister strip drive mechanism including a blister strip drive member shaped to contact the strip along a line defined by the crease between a blister pocket and said surface, to drive said strip.

14 Claims, 6 Drawing Sheets

(51) Int. Cl.
*A62B 7/00* (2006.01)
*A62B 9/00* (2006.01)

(56) References Cited

U.S. PATENT DOCUMENTS

| | | | |
|---|---|---|---|
| 7,878,196 B2* | 2/2011 | Pocock et al. | 128/203.21 |
| 8,020,554 B2* | 9/2011 | Pocock et al. | 128/203.21 |
| 8,069,850 B2* | 12/2011 | Pocock et al. | 128/203.21 |
| 8,087,411 B2* | 1/2012 | Pocock et al. | 128/203.21 |
| 8,261,740 B2* | 9/2012 | Pocock et al. | 128/203.15 |
| 8,322,336 B2* | 12/2012 | Pocock et al. | 128/203.15 |
| 8,336,542 B2* | 12/2012 | Anderson et al. | 128/202.22 |
| 2002/0032409 A1* | 3/2002 | Ritsche | 604/154 |
| 2004/0099676 A1* | 5/2004 | Anderson et al. | 221/25 |
| 2005/0081853 A1* | 4/2005 | Young et al. | 128/203.21 |
| 2005/0087188 A1* | 4/2005 | Young et al. | 128/203.15 |
| 2005/0154491 A1 | 7/2005 | Anderson et al. | |
| 2005/0174216 A1 | 8/2005 | Lintell | |
| 2005/0274378 A1* | 12/2005 | Bonney et al. | 128/200.23 |
| 2006/0196504 A1* | 9/2006 | Augustyn et al. | 128/203.15 |
| 2007/0062525 A1* | 3/2007 | Bonney et al. | 128/203.21 |
| 2007/0137645 A1* | 6/2007 | Eason et al. | 128/203.15 |
| 2008/0099016 A1 | 5/2008 | Pocock et al. | |
| 2009/0007907 A1* | 1/2009 | Eason et al. | 128/203.15 |
| 2009/0007908 A1* | 1/2009 | Eason et al. | 128/203.15 |
| 2009/0151722 A1* | 6/2009 | Eason et al. | 128/203.15 |
| 2010/0012119 A1* | 1/2010 | Sallak et al. | 128/203.15 |
| 2010/0258118 A1* | 10/2010 | Morton | 128/203.15 |
| 2010/0288278 A1* | 11/2010 | Pocock et al. | 128/203.21 |
| 2011/0132358 A1 | 6/2011 | Eason et al. | |

FOREIGN PATENT DOCUMENTS

| | | |
|---|---|---|
| CN | 101107034 A | 1/2008 |
| EP | 0467172 A1 | 1/1992 |
| EP | 0469814 A1 | 2/1992 |
| EP | 1132104 A2 | 9/2001 |
| FR | 2667790 | 4/1992 |
| WO | 03/061743 A1 | 7/2003 |
| WO | WO 03092576 A | 11/2003 |
| WO | 2005/037353 A1 | 4/2005 |
| WO | 2006/079749 A2 | 8/2006 |
| WO | 2007/096111 A2 | 8/2007 |
| WO | 2007/134792 A1 | 11/2007 |

OTHER PUBLICATIONS

Written Opinion of the international Searching Authority issued in connection with International Patent Application No. PCT/EP2009/050730.

Office Action, dated Oct. 12, 2012, issued by the Chinese Patent Office in connection with corresponding Chinese Patent Application No. 200980110498.4.

* cited by examiner

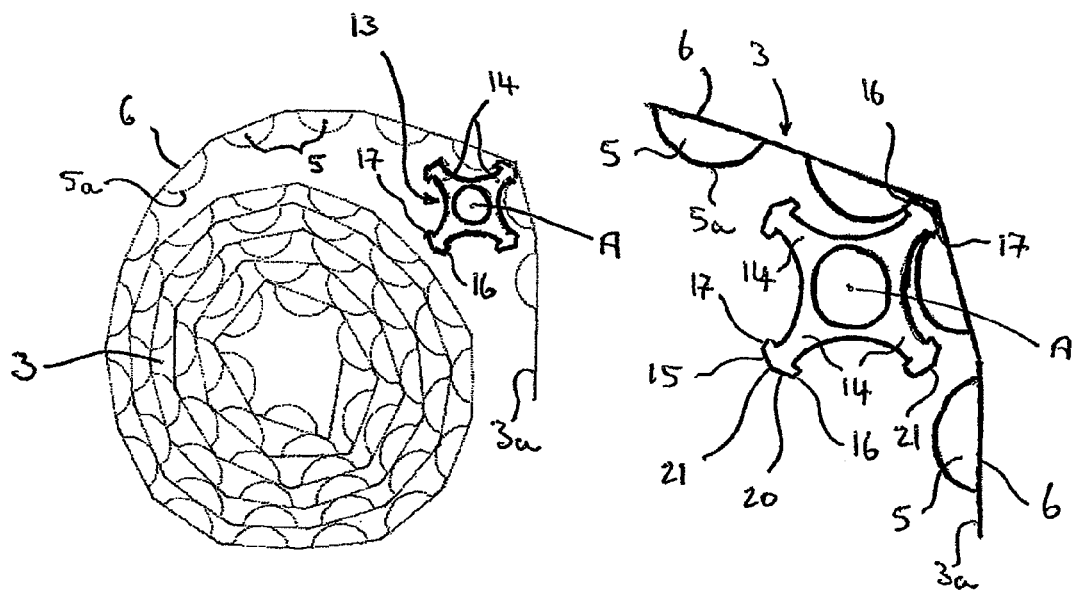
FIGURE 3A
(PRIOR ART)
FIGURE 3b
(PRIOR ART)
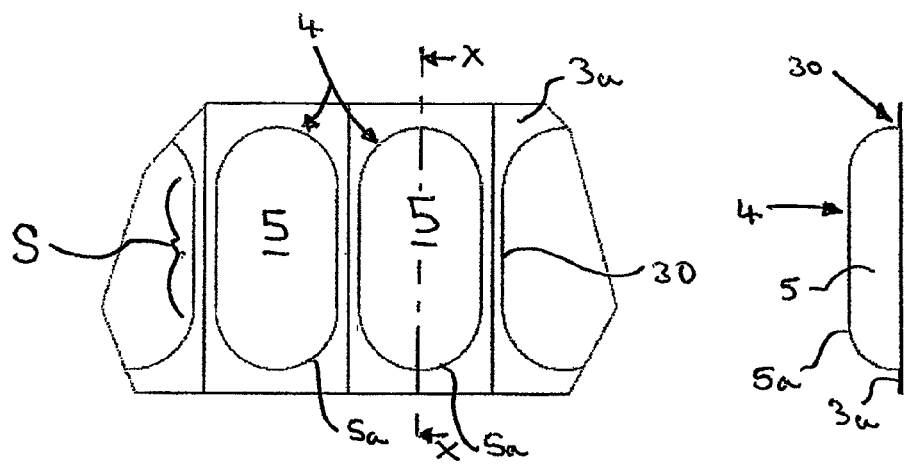
FIGURE 4A
(PRIOR ART)
FIGURE 4B
(PRIOR ART)

8,944,055 B2

INHALER

This application is a national phase application under 35 U.S.C. §371 of International Application No. PCT/EP2009/050730, filed Jan. 22, 2009, which claims priority to European Patent Application No. EP 08100881.5, filed Jan. 24, 2008, the disclosures of which are all hereby incorporated by reference herein.

The present invention relates to an inhalation device for oral or nasal delivery of medicament in powdered form. More specifically, the invention relates to an inhaler having a housing to receive a blister strip having a plurality of blister pockets spaced along the length of the strip, each blister pocket having a puncturable lid and containing a dose of medicament for inhalation by a user. The invention also relates to an inhaler containing a blister strip each having a puncturable lid and containing a dose of medicament for inhalation by a user of the device according to the invention.

Oral or nasal delivery of a medicament using an inhalation device is a particularly attractive method of drug administration as these devices are relatively easy for a patient to use discreetly and in public. As well as delivering medicament to treat local diseases of the airway and other respiratory problems, they have more recently also been used to deliver drugs to the bloodstream via the lungs, thereby avoiding the need for hypodermic injections.

It is common for dry powder formulations to be pre-packaged in individual doses, usually in the form of capsules or blisters which each contain a single dose of the powder which has been accurately and consistently measured. A blister is generally cold formed from a ductile foil laminate or a plastics material and includes a puncturable or peelable lid which is permanently heat-sealed around the periphery of the blister during manufacture and after the dose has been introduced into the blister. A foil blister is preferred over capsules as each dose is protected from the ingress of water and penetration of gases such as oxygen in addition to being shielded from light and UV radiation all of which can have a detrimental effect on the delivery characteristics of the inhaler if a dose becomes exposed to them. Therefore, a blister offers excellent environmental protection to each individual drug dose.

Inhalation devices that receive a blister pack comprising a number of blisters each of which contain a pre-metered and individually packaged dose of the drug to be delivered are known. Actuation of the device causes a mechanism to breach or rupture a blister, such as by puncturing it or peeling the lid off, so that when the patient inhales, air is drawn through the blister entraining the dose therein that is then carried out of the blister through the device and via the patient's airway down into the lungs. Pressurized air or gas or other propellants may also be used to carry the dose out of the blister. Alternatively, the mechanism that punctures or opens the blister may push or eject the dose out of the blister into a receptacle from which the dose may subsequently be inhaled.

It is advantageous for the inhaler to be capable of holding a number of doses to enable it to be used repeatedly over a period of time without the requirement to open and/or insert a blister into the device each time it is used. Therefore, many conventional devices include means for storing a blister strip having a number of blister pockets spaced along the length of the strip, each blister pocket containing an individual dose of medicament. Such devices also include an indexing mechanism for driving the strip so as to move an emptied blister pocket away from the opening mechanism so that a fresh one is moved into alignment with the opening mechanism so that it is in position ready to be opened for inhalation of its contents.

An inhaler of the type described above is known from the Applicant's own co-pending international application no. PCT/GB2004/004416 filed on 18 Oct. 2004 and claiming priority from GB0324358.1 filed 17 Oct. 2003. This international application has been published as WO2005/037353 A1.

According to one embodiment described and claimed in WO 2005/037353 A1, and illustrated in FIGS. 1a and 1b of the accompanying drawings, an inhaler 1 has a housing 2 containing a strip 3 having a plurality of individually spaced moisture proof blisters 4 each containing a pre-measured dose of powdered medicament for inhalation coiled up within the housing 2. Each blister 4 of the strip 3 comprises a pocket 5 having a wall 5a and a flat puncturable lid 6 permanently heat sealed to the pocket 5 to hermetically seal the dose therein. The strip 3 is preferably manufactured from foil laminate, such as aluminium, and plastics material. Although the wall 5a of the pockets 5 may be hemispherical in shape, they often take the form of one half of a capsule that essentially has a tubular central portion with hemispherically shaped ends. The "capsule" is halved along its major axis so as to provide the resulting half-capsule or "hemi-capsule" shaped blister pocket 5 with a flat, open, top to which the puncturable lidding material 6 is applied after a dose has been deposited in the pocket 5. A portion of a blister strip 3 showing a cross-section through one blister pocket 5 and a plan view showing two blister pockets having this more elongate rather than rounded shape is shown in FIGS. 4a and 4b.

The inhaler known from WO 2005/037353 A1 comprises an indexing or blister strip drive mechanism 7 having an actuating lever 8 that moves the strip 3 over a blister locating chassis 9 to successively align each blister pocket 5 with a blister piercing element 10, when the actuator 8 is pivoted in a direction indicated by arrow "A" in FIG. 1b. The blister pocket 5c (see FIG. 2) that has been aligned with the blister piercing element 10 is pierced on the return stroke of the actuator 8 (in the direction indicated by arrow "B" in FIG. 1b) by the piercing elements 10 on the actuator 8 so that, when a user inhales through a mouthpiece 12, an airflow is generated within the blister pocket 5 to entrain the dose contained therein and carry it out of the blister pocket 5 via the mouthpiece 12 and into the user's airway.

It will be appreciated that the indexing mechanism 7 is required to provide good and repeatable positional accuracy as the blister strip 3 is indexed through the inhaler 1 so that every blister pocket 5 of the strip 3 is aligned with the blister piercing element 10, one after the other. The indexing mechanism 7 must also be capable of transmitting relatively high driving forces to drive the strip 3 to overcome resistance within the inhaler 1 which is caused, for example, by moving or unwinding a long, possibly tightly coiled strip 3 and because of the need to overcome frictional forces which may increase as a result of any residual powder dose within the inhaler 1 that has not been inhaled but has escaped from opened blister pockets 5 and which covers the strip 3 or components of the indexing mechanism 7.

In the embodiments disclosed in WO 2005/037353 A1, the indexing mechanism 7 includes an indexing wheel 13 mounted for rotation about an axis marked "A" and having four spokes 14 with enlarged head portions 15. This conventional drive wheel is more clearly illustrated in FIG. 3. Each enlarged head portion 15 has a flat leading face 16 and a flat trailing face 17. The blister strip 3 passes around the indexing wheel 13 and individual blister pockets 5 are held between adjacent spokes 14. As the drive wheel 13 rotates (in an anticlockwise direction as shown in FIGS. 1 and 2 but clockwise in FIGS. 3A and 3B), the strip 3 is indexed forward, in a direction indicated by arrow marked "C" as the flat leading face 16 of the head portion 12 contacts and pushes against the curved surface 5a of the blister pocket 5 which is positioned between adjacent spokes 14. The interaction of the drive wheel and the blister being driven therefore controls the end position of the next blister to be pierced, i.e. the accuracy of its actual to its nominal indexed position.

It will be appreciated that the wall 5a of the blister pocket 5 is formed from a relatively thin-walled soft and flexible material such as aluminium foil laminated with PVC and nylon layers, and it has been found that, as driving forces increase, blister pockets 5 can be deformed or damaged as a result of the pressure applied to them by the flat leading face 16. It is also common for individual blister pockets 5 on the same strip 3 to exhibit some variation in size and shape due to manufacturing tolerances which can also cause a blister pocket 5 to pop out of engagement with the indexing wheel 13 or alter the point of contact of the spoke 14 against the blister pocket 5 resulting in a reduction in the ability to achieve repeatable positional accuracy.

It is also known from the prior art to provide an inhalation device with an indexing mechanism that includes a drum with blister shaped concavities or recesses rather than a spoked wheel. However, the drum must be made to very precise tolerances to ensure a good fit between the recess and the blister pocket. Furthermore, because of the inevitable tolerance in both, the actual points of contact of the recess with the blister pocket cannot be determined with any certainty and may change from blister pocket to blister pocket. If there are few points of contact for certain blisters, the forces can become highly concentrated over a small surface area of a blister pocket and can be sufficient to cause the blister pocket to deflect or deform. Positional accuracy also remains a problem as driving forces increase.

It is also known from the prior art to provide an indexing mechanism that includes a sprocket wheel that is configured to engage with a series of sprocket holes or slots extending along the length of the strip. Although this enables relatively high drive forces to be transmitted to the strip, the strip is more complicated to manufacture, as it requires the sprocket holes or slots to be punched or otherwise cut out of the strip. If the punched out material is not fully removed from the strip it could become detached during indexing and subsequent inhalation which could cause a choking hazard or other complications if inhaled together with a dose. Furthermore, as the indexing feature controls the end position of the next blister to be pierced, indexing in this way on a feature other than the blister represents an additional tolerance on the index position. This must be minimised by ensuring that the tolerances between the hole and the blister pocket are accurately controlled, otherwise the strip may become misaligned as it is indexed through the inhaler. Finally, it is important to ensure that the sprocket holes are spaced at least a minimum distance from the blister pockets otherwise the ability of the strip to prevent moisture ingress into the blister pocket may be compromised.

The present invention seeks to overcome or at least substantially alleviate the problems described above and provide an indexing mechanism that directly drives the blisters without placing undue loading on the blister pocket.

According to the present invention, there is provided an inhaler comprising a housing to receive a strip having a surface and a plurality of blister pockets depending from said surface, each blister pocket containing a dose of medicament for inhalation by a user and, a blister strip drive mechanism including a blister strip drive member shaped to contact the strip along a line defined by the crease between a blister pocket and said surface, to drive said strip.

In a most preferred embodiment, the blister strip drive member is configured to direct a larger component of force in a direction along the surface of the strip relative to a component of force directed against a blister pocket.

As the force is applied to the strip along a line defined by the crease between a blister pocket and the surface of the strip i.e. to the "root" of the blister pocket, a much greater component of the force extends along the length of the strip rather than against the curved surface of an individual blister pocket with which a prior art drive member comes into contact.

The blister drive mechanism preferably includes an arm and the blister strip drive member is disposed on an end of said arm.

In a preferred embodiment, the blister strip drive member has a blister strip contact edge to contact the strip along said line defined by the crease between a blister pocket and said surface.

The edge may have a radius of up to 0.2 mm, with the smallest possible radius being preferred.

In one embodiment, the blister strip drive member comprises an enlarged head on the end of the arm that tapers from the arm to the blister strip contact edge.

Advantageously, the blister strip drive member and arm are configured so that the only contact of the drive mechanism with the blister strip is with the blister strip contact edge.

In one embodiment, the head can be arcuate in shape such that the blister strip contact edge contacts a curved line defined by the crease between a hemispherically shaped blister pocket and the surface of the strip. It will be appreciated that if the head is arcuate in shape, then the arm may also have a similar shape as well, although this is not essential.

It will also be appreciated that the blister pockets may take many different shapes or forms. What is important is that the head profile is such that its blister strip contact edge matches the shape of the crease or root between the blister pockets and the surface of the strip, irrespective of whether that crease is curved, partially curved or straight or a combination of these.

Preferably, the blister strip drive member has leading and trailing blister strip contact edges on opposite sides of an axis extending in a radial direction through said arm and the blister strip drive member so that the leading blister strip contact edge contacts the strip along said line defined by the crease between one blister pocket and said surface when the drive member is rotated in one direction and so that the trailing blister strip contact edge contacts the strip along said line defined by the crease between an adjacent blister pocket and said surface, when the drive member is rotated in the opposite direction. This reverse drive capability is useful, for example, if the device needs to be able to recover from partial indexing where the user might return the lever after only incomplete operation, in which case the strip needs to be returned to its start position.

A side view of the blister strip drive member is substantially triangular or part triangular in shape, the apex of the triangle pointing in a radially inward direction along the length of the arm.

The blister strip drive member can have a substantially flat or concave end face extending between said blister strip contact edges. The substantially flat or concave shaped end face may extend in a plane lying substantially at right angles to a plane of the arm.

In a preferred embodiment, the distance between said leading and trailing edges of the blister strip contact edges in a direction along the end face is selected so as to be substantially the same as the distance between the crease of adjacent blister bowls of a blister strip to be indexed.

In a further embodiment, the pitch of the drive wheel is selected so as to be larger than the pitch of the blister strip. In this case, the pitch of the drive wheel is the chord length plus the tip width (W1+W2).

The drive mechanism may be configured to sequentially move a blister into alignment with a blister opening member.

In a preferred embodiment, the inhaler comprises a mouthpiece and a cap to cover the mouthpiece, the drive mechanism being operable in response to movement of the cap by a user.

The inhaler may alternatively comprise an actuator and the drive mechanism may be operable in response to movement of the actuator by a user.

In a preferred embodiment, the drive mechanism is a rotary mechanism and so includes a drive wheel. In which case, the drive wheel ideally comprises a plurality of spokes, each spoke forming an arm of the blister drive mechanism. It will also be appreciated that the drive mechanism may take other forms such as linear, rather than rotary.

Preferably, the drive wheel is rotatable to move the arm so that the blister strip drive member contacts a strip along a line defined by the crease between a blister pocket and said surface of the strip, to drive said strip.

In one embodiment, the inhaler comprises a blister strip having a surface and a plurality of blister pockets depending from said surface, each blister pocket containing a dose of medicament for inhalation by a user, contained within said housing.

Each blister pocket may have a part cylindrical central region and part hemispherical end regions. In this case, the blister strip contact edge may be shaped so as to have a central straight section with curved end sections or, it may just be straight, in which case it just contacts the central straight section formed from the part cylindrical central section of the blister pocket. However, it will be appreciated that the blister pocket may take any shape and the blister strip contact edge may be shaped to suit.

In a preferred embodiment, the distance between the creases of adjacent blister bowls is substantially the same as the distance between the leading and trailing edges of the blister strip contact edges.

In another preferable embodiment, the pitch of the blister strip is selected so that it is less than the pitch of the drive wheel.

Embodiments of the invention will now be described, by way of example only, with reference to FIGS. 5 and 6 of the accompanying drawings, in which:—

FIGS. 1 and 2 are side views of a conventional inhalation device to show how a strip is driven to sequentially move blisters into alignment with a blister piercing element by movement of an actuator from the position shown in FIG. 1 to the position shown in FIG. 2 which drives an indexing wheel. A piercing element on the actuator pierces the lid of an aligned blister when the actuator is returned to its normal position, as shown in FIG. 1;

FIG. 3a shows a view of the conventional indexing wheel used in the inhalation device shown in FIGS. 1 and 2;

FIG. 3b shows a partial, enlarged view of the indexing wheel shown in FIG. 3a;

FIG. 4a shows a bottom plan view of a section of blister strip showing two blister pockets and FIG. 4b shows a cross-section through one of the blister pockets shown in FIG. 4a, taken along the line X-X;

FIG. 5a shows an enlarged partial view of an indexing wheel according to an embodiment of the present invention;

FIG. 5b shows a partial, enlarged view of the indexing wheel shown in FIG. 5a;

The conventional inhalation device shown in FIGS. 1 and 2 has already been described in detail above and so no further reference to it will be made here.

Figure 1:
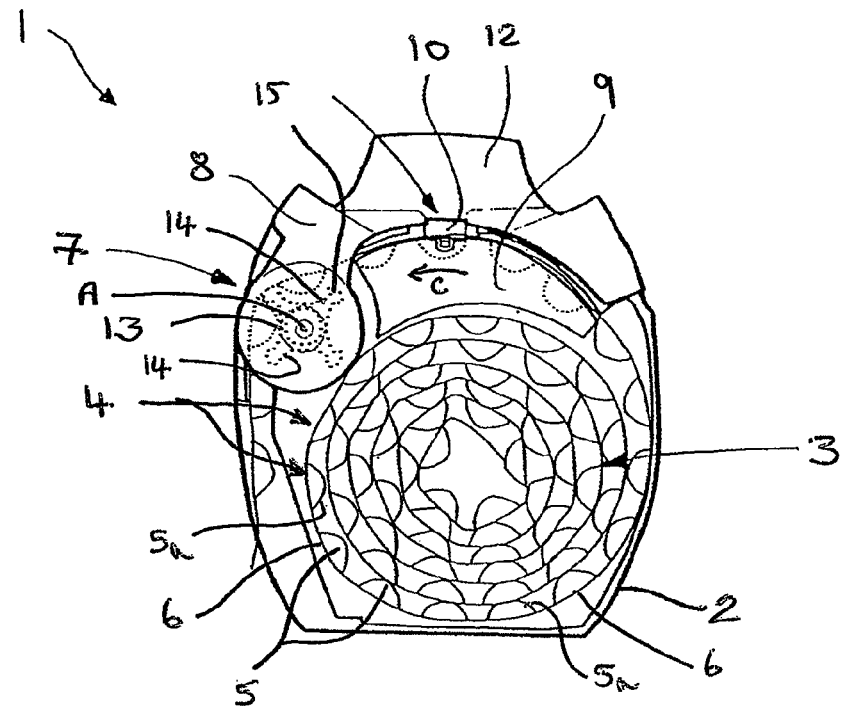
Figure 2:
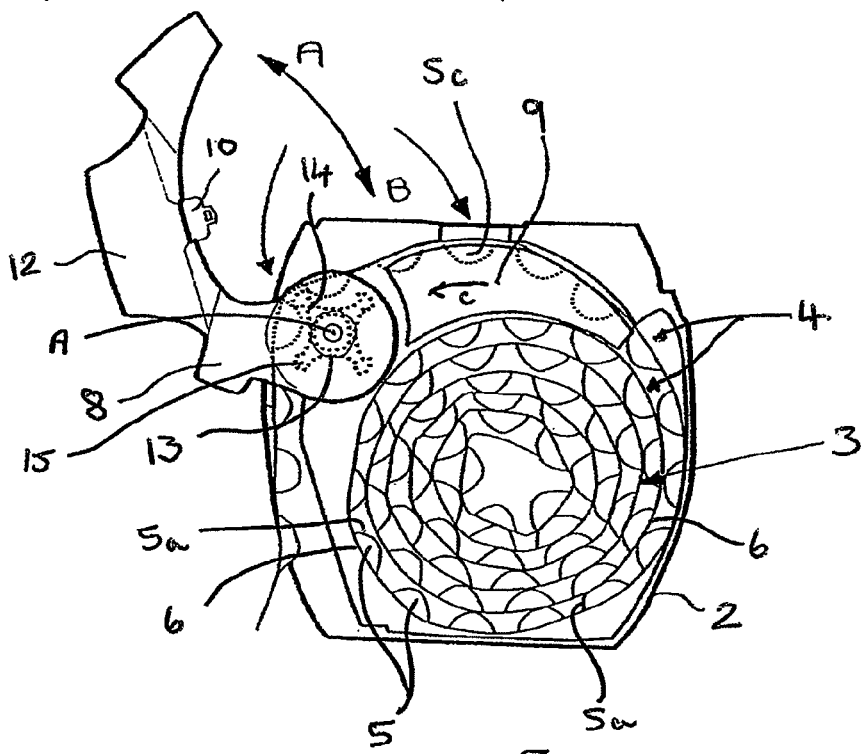

Referring first to FIGS. 3a and 3b, there is shown an enlarged view of the blister strip drive wheel 13 forming part of the indexing mechanism 7 of the device shown in FIGS. 1 and 2.

As can be seen from FIGS. 3a and 3b, the conventional blister indexing wheel 13 has four spokes 14 with enlarged head portions 15 having a flat leading face 16 that contacts the curved wall 5a of a blister pocket 5 to drive the strip 3, and gently sloping upper end faces 20 that converge to an apex 21.

The strip 3 passes around the drive wheel 13 and individual blister pockets 5 are held between adjacent spokes 14. As the drive wheel 13 rotates, the strip 3 is indexed forward, in a direction indicated by arrow marked "B" as the flat leading face 16 of the head portion 15 of a spoke 14 contacts and pushes against the curved surface 5a of the blister pocket 5 which is positioned between adjacent spokes 11. Consequently, the load is entirely applied to the curved wall 5a of the blister pocket 5, over the area of contact of the flat leading face 16 with the curved blister pocket wall 5a, which can result in deformation or buckling of the blister pocket wall 5a, especially when relatively high driving loads are required to overcome friction or other resistance.

Figures 5A, 5B:
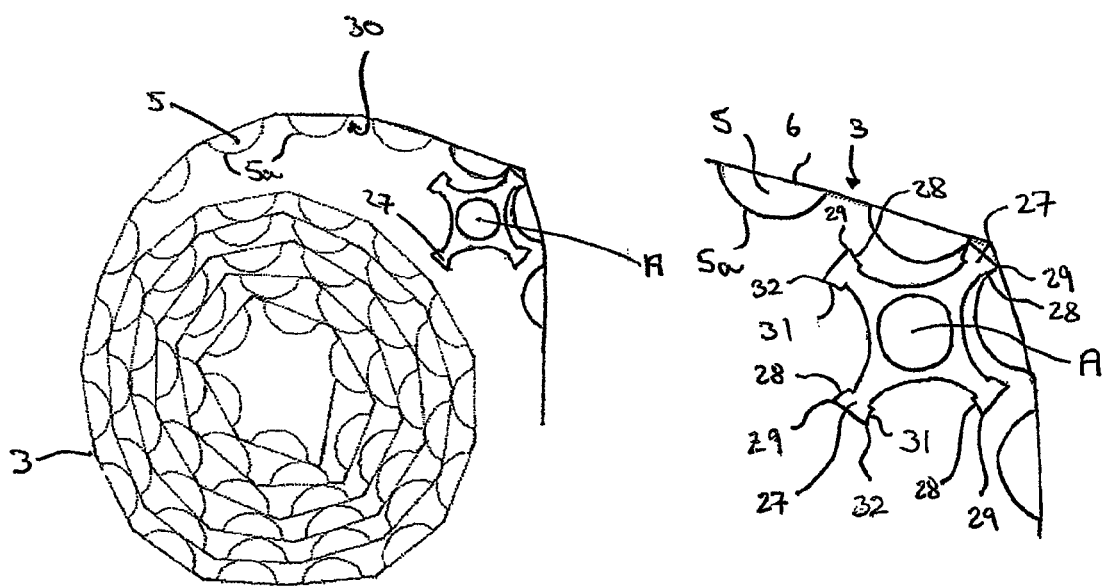

Referring now to FIGS. 5a and 5b, there is shown a drive wheel 25, according to an embodiment of the present invention. The drive wheel 25 has the same general form as the conventional drive wheel 13 described above, except that the head portion or blister strip drive member 27 of each spoke 26 has a different shape so that it contacts a different part of the strip 3.

The blister strip drive member 27 has a leading edge 29 with a non-contacting face 28 which is angled so that it does not come into contact with the curved wall surface 5a of the blister pocket 5. Instead, the region of contact with the blister strip 3 is along a line or edge 29 at the outermost tip of the non-contacting face 28, the non-contacting face 28 itself does not contact the strip 3 or the pocket 5. The edge 29 contacts the blister strip 3 in the crease 30 or junction between the underside surface 3a of the blister strip 3 and the blister pocket 5 depending from that surface 3a, rather than contacting the curved wall surface 5a of the blister pocket 5 away from the surface 3a. The non-contacting face 28 effectively tapers or narrows towards the edge 29 due to the angle of the non-contacting face 28. The edge 29 may have a radius of less than 0.2 mm to fit into the crease between the blister pocket 5 and the surface 5a, although not so sharp as to cut the blister. Load to the strip is therefore applied through the root of the blister pocket between the blister wall 5a and the surface of the strip 3a, this being a much stronger part of the strip 3 than the wall 5a.

Although the drive wheel 25 can be configured to convey the strip 3 in only one direction, in which case the non-contacting face 28 and edge 29 need only be formed so that the edge 29 contacts a blister strip 3 as the drive wheel 25 rotates on one direction, it will also be appreciated that the drive wheel 25 may also be used to interchangeably drive the strip in either direction to, for example, return the strip 3 to its original position on an "abort stroke" in which a blister pocket 5 is not opened. Therefore, in addition to the non-contacting face 28 and edge 29, there may also be a trailing non-contacting face 31 and associated edge 32. The edge 32 will then engage the strip 3 in the crease 30 formed between the blister pocket 5 and the surface 3a of the blister pocket immediately behind the blister pocket 5 that was engaged by the edge 29 of the non-contacting face 28 during rotation in the normal direction to index the strip 3, when the drive wheel 25 rotates in the opposite direction. Each spoke 26 of the drive member 25 may be symmetrical about an axis extending in a radial direction along the length of the spoke 26 and through the blister strip drive member 27.

The present invention is intended primarily for use with blister strips 3 in which the blister pockets 5 are so shaped that the crease 30 between the blister pocket 5 and the surface 3a of the strip 3 has a straight portion, generally indicated by "S" in FIG. 4a, extending between two curved portions at either end. The blister drive member 27 can then contact the blister strip 3 along said straight portion of the crease 30 between the curved ends in the region marked "S".

However, it is also envisaged that the invention could also be used with a blister strip 3 in which the blister pockets 5 are hemispherically shaped. In this case, each spoke 26 and blister drive member 27 can have a curved or arcuate shape so as to match the curved shape of the crease 30 between the hemispherically shaped blister pocket and the surface of the strip 3. As mentioned above, the blister pockets 5 can take different forms and the spoke 26 and/or the blister drive member 27 can be correspondingly shaped so as to make line contact with the root or crease 30 between the blister pocket 5 and the surface of the blister strip 3.

Although reference is made to a drive wheel 25 that rotates to drive the blister strip 3, it will be appreciated that the drive mechanism may take other forms and include reciprocating or sliding components, i.e. a linear rather than rotary mechanism. Only the portion that actually contacts the blister strip 3 or, more specifically, the crease between the blister pocket 5 and the surface 3a of the blister strip 3 needs to have the shape and/or configuration so as to provide edge contact of the blister drive member with the crease.

Figure 6:
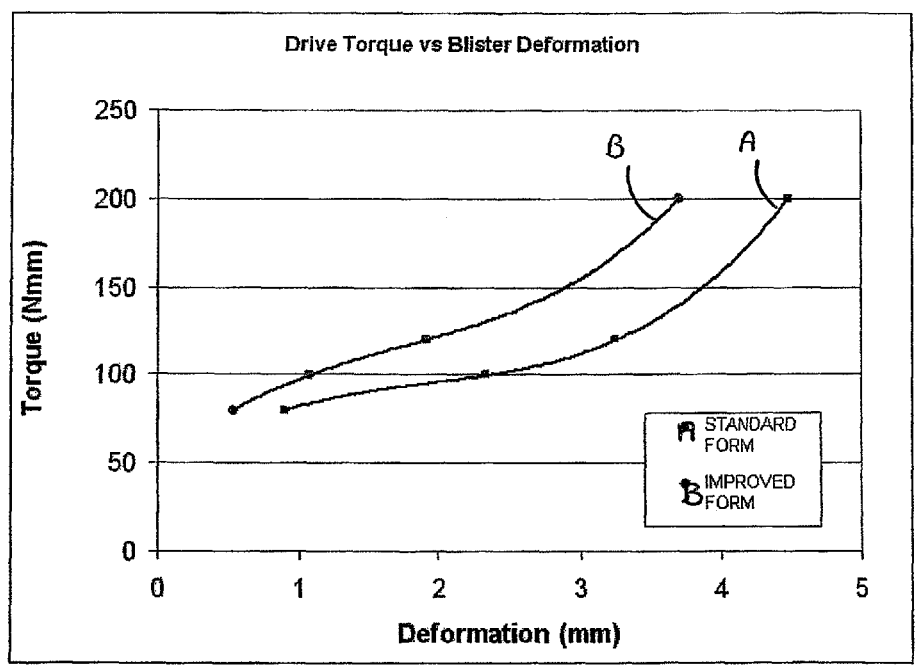
FIG. 6 shows a torque/blister deformation curve when both a conventional drive mechanism and, a drive mechanism modified according to the present invention, is used, to demonstrate how a much greater drive torque and thereby a greater force may be applied to the strip using the blister drive member of the present invention before deformation of the blister pocket occurs.

It has been found by experiment that by applying load to the strip 3 by making line contact with the crease or junction 30 between the pocket 5 and the surface 5a of the strip 3, the load, or at least a greater component of the load, is distributed along the plane of the strip 3 as opposed to a greater component of the load being concentrated on a contact area on the wall 5a of the pocket 5. Therefore, the strip 3 can withstand much higher driving forces without buckling, deformation or damage to the blister pocket 5. This improvement is demonstrated with reference to FIG. 6 of the drawings which illustrates a graph to compare the drive torque against deformation when load is applied to a strip 3 using a conventional drive mechanism (line "A"), as opposed to the drive mechanism of the present invention (line "B") in which load is applied to the strip 3 at the junction 30 between the blister pocket 5 and the surface 3a. As can be seen from the graph, much more deformation of the blister pocket 5 is evident with the conventional mechanism than with the new mechanism at the same level of torque. In fact, the graphs show more than double the blister deformation for the conventional mechanism than compared to the new mechanism at a torque in the region of 100 Nmm.

It will be appreciated that the blister strip drive mechanism may be employed with many different types of inhalation device containing a strip of blisters which are driven through the device. In particular, it can be used with the device known from the Applicant's own earlier application now published as WO 2005/037353 A1. A particular advantage when used in a device such as the one disclosed in this document is that it provides a greater resistance to "pull-through", i.e. where the user attempts to pull on the strip emerging from the housing. It is also applicable to a fully-integrated type of device where the used blisters are retained and coiled-up within the housing in, for example, a spiral wound element known from the Applicants own earlier EP application No. 07111998.6. In this case, the drive mechanism of the invention provides additional drive torque to drive the strip into the used strip wind-up device or mechanism.

It has also been established that by careful selection of the geometry of the wheel tip, variability in the final strip position when indexing the strip is reduced and consistency in strip position when indexing backwards during an "abort stroke" is improved. Furthermore, the shape of the drive wheel may be carefully controlled so as to maximise the available drive torque to the blister strip.

Figure 7:
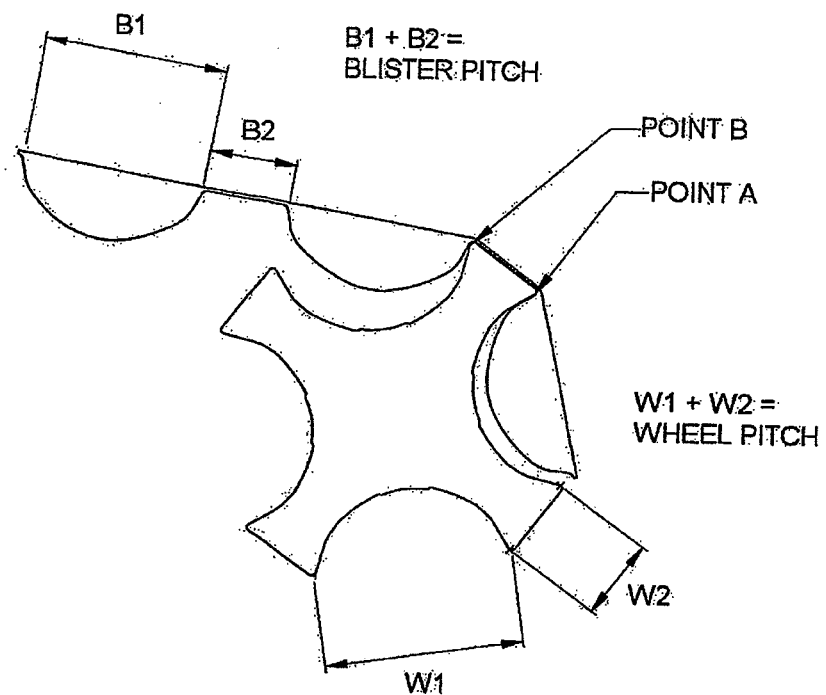
FIG. 7 shows a drive wheel with a blister strip extending around it to emphasise the importance of the relative geometry of the blister strip and drive wheel, the strip passing over the wheel which is rotating in a clockwise direction.

Referring initially to FIG. 7, it has been found that by reducing the clearance between the tip of the drive wheel and the roots of the blisters, at point A and B in FIG. 7, the blisters wrap tightly around the drive wheel tip, thereby minimising any backlash (movement of the indexing wheel whilst the strip remains stationary) when the direction of rotation of the drive wheel is reversed.

A system with no backlash allows the blisters to be positioned in the same place when driven forwards or backwards. A nominal wheel tip width, W2 (see FIG. 7), equal to the distance between blisters, B2, has been proved to work effectively.

It has also been determined that the pitch of the drive wheel namely, the chord length plus the tip width (W1+W2) relative to the pitch of the blister strip namely, blister width plus blister separation (B1+B2), is critical to the level of available drive torque before plastic deformation of the blister bowl occurs.

Figure 8:
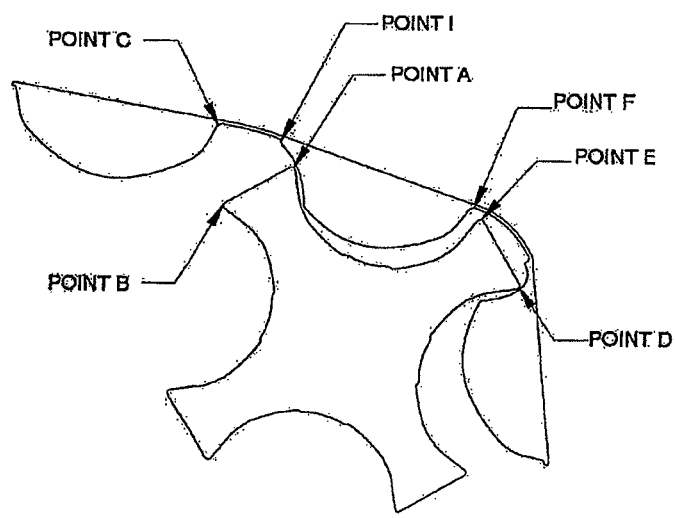
FIG. 8 shows a drive wheel with a blister strip extending around it in which the pitch of the drive wheel is equal to the blister pitch, the drive wheel rotating in a clockwise direction.

When considering a single blister bowl, the force required from the drive wheel to deform the blister bowl increases as the deflection of the blister wall increases, until such deflection causes the wall of the blister bowl to reach its plastic deformation limit. When the blisters are being indexed by a drive wheel of equal pitch to the blisters, i.e. W1=B1 and W2=B2, a small amount of deflection of the driven blister (at point D in FIG. 8) leads to a situation where blister deflection, or plastic blister deformation of the next blister to be indexed, point A, occurs, and hence this deflection propagates to the next blister to be driven by the drive wheel, leading to cumulative denting and eventual failure of the drive system.

Figure 9:
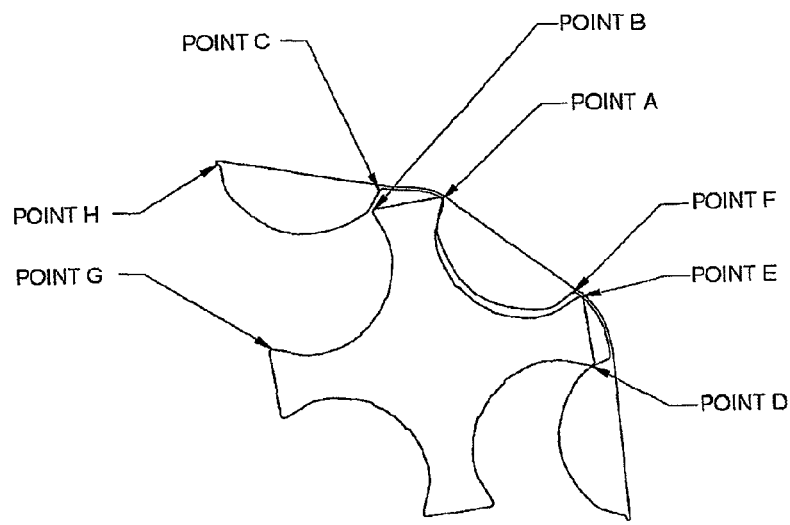
FIG. 9 shows a drive wheel with a blister strip extending around it in which the pitch of the drive wheel is greater than the blister pitch, the drive wheel rotating in a clockwise direction.

To avoid the aforementioned problem, the wheel pitch (W1+W2) is increased in relation to the blister pitch (B1+B2) and a drive system capable of indexing a larger load without dent propagation to the blister bowl is achieved. If deflection of the blister at a point D occurs (see FIG. 9), the leading wheel tip of the next vane, point A, will contact the blister at a point closer to the root of the blister, thereby minimising denting or deformation of the blister bowl. This effect can be seen in the graph of FIG. 10 and which shows that for a drive wheel having a pitch greater than the blisters by 0.8 mm, a drive force of 13N can be achieved with 45 µm aluminium foil, whereas with a difference in pitch of only 0.1 mm, a drive force of just 2.5N can be achieved with the same foil.

Figure 10:
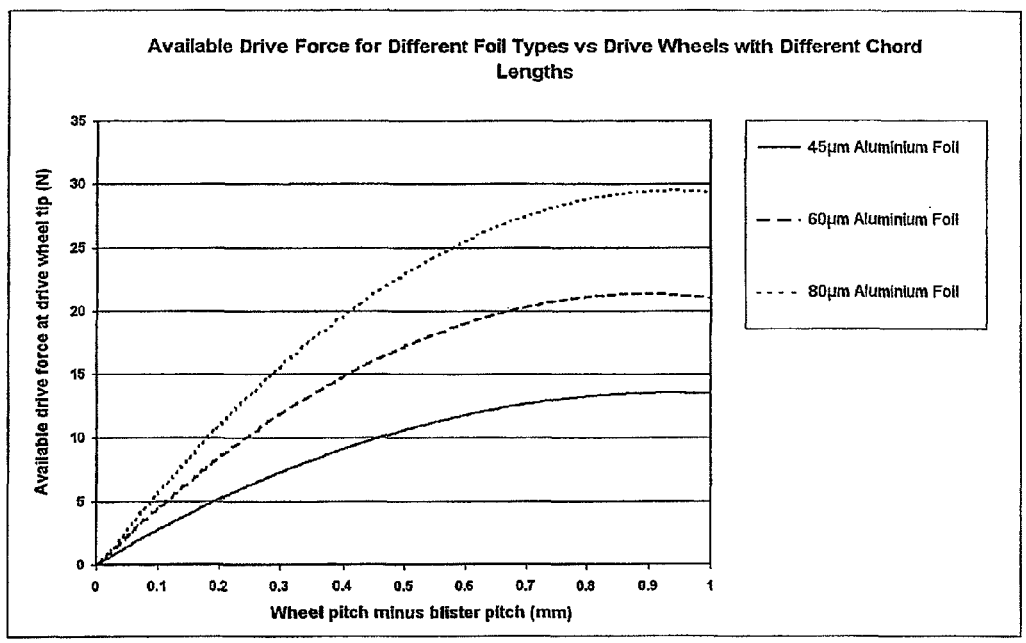
FIG. 10 is a graph to show the relationship between the wheel and blister pitch values and the transmissible torque for various blister foil thickness.

It will be appreciated that the blister pockets are the weakest component in the drive system. Therefore, the thickness of the aluminium laminate layer, and hence the strength of the blisters, has a direct relationship to the strength of the drive system, as shown in FIG. 10. The graph shows that by increasing the thickness of the laminate, the ability of the drive to index a greater load is increased.

Many modifications and variations of the invention falling within the terms of the following claims will be apparent to those skilled in the art and the foregoing description should be regarded as a description of the preferred embodiments of the invention only.

A variety of medicaments may be administered alone by using inhalers of the invention. Specific active agents or drugs that may be used include, but are not limited to, agents of one or more of the following classes listed below.

1) Adrenergic agonists such as, for example, amphetamine, apraclonidine, bitolterol, clonidine, colterol, dobutamine, dopamine, ephedrine, epinephrine, ethylnorepinephrine, fenoterol, formoterol, guanabenz, guanfacine, hydroxyamphetamine, isoetharine, isoproterenol, isotharine, mephenterine, metaraminol, methamphetamine, methoxamine, methpentermine, methyldopa, methylphenidate, metaproterenol, metaraminol, mitodrine, naphazoline, norepinephrine, oxymetazoline, pemoline, phenylephrine, phenylethylamine, phenylpropanolamine, pirbuterol, prenalterol, procaterol, propylhexedrine, pseudoephedrine, ritodrine, salbutamol, salmeterol, terbutaline, tetrahydrozoline, tramazoline, tyramine and xylometazoline.

2) Adrenergic antagonists such as, for example, acebutolol, alfuzosin, atenolol, betaxolol, bisoprolol, bopindolol, bucindolol, bunazosin, butyrophenones, carteolol, carvedilol, celiprolol, chlorpromazine, doxazosin, ergot alkaloids, esmolol, haloperidol, indoramin, ketanserin, labetalol, levobunolol, medroxalol, metipranolol, metoprolol, nebivolol, nadolol, naftopidil, oxprenolol, penbutolol, phenothiazines, phenoxybenzamine, phentolamine, pindolol, prazosin, propafenone, propranolol, sotalol, tamsulosin, terazosin, timolol, tolazoline, trimazosin, urapidil and yohimbine.

3) Adrenergic neurone blockers such as, for example, bethanidine, debrisoquine, guabenxan, guanadrel, guanazodine, guanethidine, guanoclor and guanoxan.

4) Drugs for treatment of addiction, such as, for example, buprenorphine.

5) Drugs for treatment of alcoholism, such as, for example, disulfiram, naloxone and naltrexone.

6) Drugs for Alzheimer's disease management, including acetylcholinesterase inhibitors such as, for example, donepezil, galantamine, rivastigmine and tacrin.

7) Anaesthetics such as, for example amethocaine, benzocaine, bupivacaine, hydrocortisone, ketamine, lignocaine, methylprednisolone, prilocaine, proxymetacaine, ropivacaine and tyrothricin.

8) Angiotensin converting enzyme inhibitors such as, for example, captopril, cilazapril, enalapril, fosinopril, imidapril hydrochloride, lisinopril, moexipril hydrochloride, perindopril, quinapril, ramipril and trandolapril.

9) Angiotensin II receptor blockers, such as, for example, candesartan, cilexetil, eprosartan, irbesartan, losartan, medoxomil, olmesartan, telmisartan and valsartan.

10) Antiarrhythmics such as, for example, adenosine, amidodarone, disopyramide, flecainide acetate, lidocaine hydrochloride, mexiletine, procainamide, propafenone and quinidine.

11) Antibiotic and antibacterial agents (including the beta-lactams, fluoroquinolones, ketolides, macrolides, sulphonamides and tetracyclines) such as, for example, aclarubicin, amoxicillin, amphotericin, azithromycin, aztreonam chlorhexidine, clarithromycin, clindamycin, colistimethate, dactinomycin, dirithromycin, doripenem, erythromycin, fusafungine, gentamycin, metronidazole, mupirocin, natamycin, neomycin, nystatin, oleandomycin, pentamidine, pimaricin, probenecid, roxithromycin, sulphadiazine and triclosan.

12) Anti-clotting agents such as, for example, abciximab, acenocoumarol, alteplase, aspirin, bemiparin, bivalirudin, certoparin, clopidogrel, dalteparin, danaparoid, dipyridamole, enoxaparin, epoprostenol, eptifibatide, fondaparin, heparin (including low molecular weight heparin), heparin calcium, lepirudin, phenindione, reteplase, streptokinase, tenecteplase, tinzaparin, tirofiban and warfarin.

13) Anticonvulsants such as, for example, GABA analogs including tiagabine and vigabatrin; barbiturates including pentobarbital; benzodiazepines including alprazolam, chlordiazepoxide, clobazam, clonazepam, diazepam, flurazepam, lorazepam, midazolam, oxazepam and zolazepam; hydantoins including phenyloin; phenyltriazines including lamotrigine; and miscellaneous anticonvulsants including acetazolamide, carbamazepine, ethosuximide, fosphenyloin, gabapentin, levetiracetam, oxcarbazepine, piracetam, pregabalin, primidone, sodium valproate, topiramate, valproic acid and zonisamide.

14) Antidepressants such as, for example, tricyclic and tetracyclic antidepressants including amineptine, amitriptyline (tricyclic and tetracyclic amitryptiline), amoxapine, butriptyline, cianopramine, clomipramine, demexiptiline, desipramine, dibenzepin, dimetacrine, dosulepin, dothiepin, doxepin, imipramine, iprindole, levoprotiline, lofepramine, maprotiline, melitracen, metapramine, mianserin, mirtazapine, nortryptiline, opipramol, propizepine, protriptyline, quinupramine, setiptiline, tianeptine and trimipramine; selective serotonin and noradrenaline reuptake inhibitors (SNRIs) including clovoxamine, duloxetine, milnacipran and venlafaxine; selective serotonin reuptake inhibitors (SSRIs) including citalopram, escitalopram, femoxetine, fluoxetine, fluvoxamine, ifoxetine, milnacipran, nomifensine, oxaprotiline, paroxetine, sertraline, sibutramine, venlafaxine, viqualine and zimeldine; selective noradrenaline reuptake inhibitors (NARIs) including demexiptiline, desipramine, oxaprotiline and reboxetine; noradrenaline and selective serotonin reuptake inhibitors (NASSAs) including mirtazapine; monoamine oxidase inhibitors (MAOIs) including amiflamine, brofaromine, clorgyline, α-ethyltryptamine, etoperidone, iproclozide, iproniazid, isocarboxazid, mebanazine, medifoxamine, moclobemide, nialamide, pargyline, phenelzine, pheniprazine, pirlindole, procarbazine, rasagiline, safrazine, selegiline, toloxatone and tranylcypromine; muscarinic antagonists including benactyzine and dibenzepin; azaspirones including buspirone, gepirone, ipsapirone, tandospirone and tiaspirone; and other antidepressants including acetaphenazine, ademetionine, S-adenosylmethionine, adrafinil, amesergide, amineptine, amperozide, benactyzine, benmoxine, binedaline, bupropion, carbamazepine, caroxazone, cericlamine, cotinine, fezolamine, flupentixol, idazoxan, kitanserin, levoprotiline, lithium salts, maprotiline, medifoxamine, methylphenidate, metralindole, minaprine, nefazodone, nisoxetine, nomifensine, oxaflozane, oxitriptan, phenyhydrazine, rolipram, roxindole, sibutramine, teniloxazine, tianeptine, tofenacin, trazadone, tryptophan, viloxazine and zalospirone.

15) Anticholinergic agents such as, for example, atropine, benzatropine, biperiden, cyclopentolate, glycopyrrolate, hyoscine, ipratropium bromide, orphenadine hydrochloride, oxitroprium bromide, oxybutinin, pirenzepine, procyclidine, propantheline, propiverine, telenzepine, tiotropium, trihexyphenidyl, tropicamide and trospium.

16) Antidiabetic agents such as, for example, pioglitazone, rosiglitazone and troglitazone.

17) Antidotes such as, for example, deferoxamine, edrophonium chloride, flumazenil, nalmefene, naloxone, and naltrexone.

18) Anti-emetics such as, for example, alizapride, azasetron, benzquinamide, bestahistine, bromopride, buclizine, chlorpromazine, cinnarizine, clebopride, cyclizine, dimenhydrinate, diphenhydramine, diphenidol, domperidone, dolasetron, dronabinol, droperidol, granisetron, hyoscine, lorazepam, metoclopramide, metopimazine, nabilone, ondansetron, palonosetron, perphenazine, prochlorperazine, promethazine, scopolamine, triethylperazine, trifluoperazine, triflupromazine, trimethobenzamide and tropisetron.

19) Antihistamines such as, for example, acrivastine, astemizole, azatadine, azelastine, brompheniramine, carbinoxamine, cetirizine, chlorpheniramine, cinnarizine, clemastine, cyclizine, cyproheptadine, desloratadine, dexmedetomidine, diphenhydramine, doxylamine, fexofenadine, hydroxyzine, ketotifen, levocabastine, loratadine, mizolastine, promethazine, pyrilamine, terfenadine and trimeprazine.

20) Anti-infective agents such as, for example, antivirals (including nucleoside and non-nucleoside reverse transcriptase inhibitors and protease inhibitors) including aciclovir, adefovir, amantadine, cidofovir, efavirenz, famiciclovir, foscarnet, ganciclovir, idoxuridine, indinavir, inosine pranobex, lamivudine, nelfinavir, nevirapine, oseltamivir, palivizumab, penciclovir, pleconaril, ribavirin, rimantadine, ritonavir, ruprintrivir, saquinavir, stavudine, valaciclovir, zalcitabine, zanamivir, zidovudine and interferons; AIDS adjunct agents including dapsone; aminoglycosides including tobramycin; antifungals including amphotericin, caspofungin, clotrimazole, econazole nitrate, fluconazole, itraconazole, ketoconazole, miconazole, nystatin, terbinafine and voriconazole; anti-malarial agents including quinine; antituberculosis agents including capreomycin, ciprofloxacin, ethambutol, meropenem, piperacillin, rifampicin and vancomycin; beta-lactams including cefazolin, cefmetazole, cefoperazone, cefoxitin, cephacetrile, cephalexin, cephaloglycin and cephaloridine; cephalosporins, including cephalosporin C and cephalothin; cephamycins such as cephamycin A, cephamycin B, cephamycin C, cephapirin and cephradine; leprostatics such as clofazimine; penicillins including amoxicillin, ampicillin, amylpenicillin, azidocillin, benzylpenicillin, carbenicillin, carfecillin, carindacillin, clometocillin, cloxacillin, cyclacillin, dicloxacillin, diphenicillin, heptylpenicillin, hetacillin, metampicillin, methicillin, nafcillin, 2-pentenylpenicillin, penicillin N, penicillin O, penicillin S and penicillin V; quinolones including ciprofloxacin, clinafloxacin, difloxacin, grepafloxacin, norfloxacin, ofloxacine and temafloxacin; tetracyclines including doxycycline and oxytetracycline; miscellaneous anti-infectives including linezolide, trimethoprim and sulfamethoxazole.

21) Anti-neoplastic agents such as, for example, droloxifene, tamoxifen and toremifene.

22) Antiparkisonian drugs such as, for example, amantadine, andropinirole, apomorphine, baclofen, benserazide, biperiden, benztropine, bromocriptine, budipine, cabergoline, carbidopa, eliprodil, entacapone, eptastigmine, ergoline, galanthamine, lazabemide, levodopa, lisuride, mazindol, memantine, mofegiline, orphenadrine, trihexyphenidyl, pergolide, piribedil, pramipexole, procyclidine, propentofylline, rasagiline, remacemide, ropinerole, selegiline, spheramine, terguride and tolcapone.

23) Antipsychotics such as, for example, acetophenazine, alizapride, amisulpride, amoxapine, amperozide, aripiprazole, benperidol, benzquinamide, bromperidol, buramate, butaclamol, butaperazine, carphenazine, carpipramine, chlorpromazine, chlorprothixene, clocapramine, clomacran, clopenthixol, clospirazine, clothiapine, clozapine, cyamemazine, droperidol, flupenthixol, fluphenazine, fluspirilene, haloperidol, loxapine, melperone, mesoridazine, metofenazate, molindrone, olanzapine, penfluridol, pericyazine, perphenazine, pimozide, pipamerone, piperacetazine, pipotiazine, prochlorperazine, promazine, quetiapine, remoxipride, risperidone, sertindole, spiperone, sulpiride, thioridazine, thiothixene, trifluperidol, triflupromazine, trifluoperazine, ziprasidone, zotepine and zuclopenthixol; phenothiazines including aliphatic compounds, piperidines and piperazines; thioxanthenes, butyrophenones and substituted benzamides.

24) Antirheumatic agents such as, for example, diclofenac, heparinoid, hydroxychloroquine and methotrexate, leflunomide and teriflunomide.

25) Anxiolytics such as, for example, adinazolam, alpidem, alprazolam, alseroxlon, amphenidone, azacyclonol, bromazepam, bromisovalum, buspirone, captodiamine, capuride, carbcloral, carbromal, chloral betaine, chlordiazepoxide, clobenzepam, enciprazine, flesinoxan, flurazepam, hydroxyzine, ipsapiraone, lesopitron, loprazolam, lorazepam, loxapine, mecloqualone, medetomidine, methaqualone, methprylon, metomidate, midazolam, oxazepam, propanolol, tandospirone, trazadone, zolpidem and zopiclone.

26) Appetite stimulants such as, for example, dronabinol.

27) Appetite suppressants such as, for example, fenfluramine, phentermine and sibutramine; and anti-obesity treatments such as, for example, pancreatic lipase inhibitors, serotonin and norepinephrine re-uptake inhibitors, and anti-anorectic agents.

28) Benzodiazepines such as, for example, alprazolam, bromazepam, brotizolam, chlordiazepoxide, clobazam, clonazepam, clorazepate, demoxepam, diazepam, estazolam, flunitrazepam, flurazepam, halazepam, ketazolam, loprazolam, lorazepam, lormetazepam, medazepam, midazolam, nitrazepam, nordazepam, oxazepam, prazepam, quazepam, temazepam and triazolam.

29) Bisphosphonates such as, for example, alendronate sodium, sodium clodronate, etidronate disodium, ibandronic acid, pamidronate disodium, isedronate sodium, tiludronic acid and zoledronic acid.

30) Blood modifiers such as, for example, cilostazol and dipyridamol, and blood factors.

31) Cardiovascular agents such as, for example, acebutalol, adenosine, amiloride, amiodarone, atenolol, benazepril, bisoprolol, bumetanide, candesartan, captopril, clonidine, diltiazem, disopyramide, dofetilide, doxazosin, enalapril, esmolol, ethacrynic acid, flecanide, furosemide, gemfibrozil, ibutilide, irbesartan, labetolol, losartan, lovastatin, metolazone, metoprolol, mexiletine, nadolol, nifedipine, pindolol, prazosin, procainamide, propafenone, propranolol, quinapril, quinidine, ramipril, sotalol, spironolactone, telmisartan, tocainide, torsemide, triamterene, valsartan and verapamil.

32) Calcium channel blockers such as, for example, amlodipine, bepridil, diltiazem, felodipine, flunarizine, gallopamil, isradipine, lacidipine, lercanidipine, nicardipine, nifedipine, nimodipine and verapamil.

33) Central nervous system stimulants such as, for example, amphetamine, brucine, caffeine, dexfenfluramine, dextroamphetamine, ephedrine, fenfluramine, mazindol, methylphenidate, modafinil, pemoline, phentermine and sibutramine.

34) Cholesterol-lowering drugs such as, for example, acipimox, atorvastatin, ciprofibrate, colestipol, colestyramine, bezafibrate, ezetimibe, fenofibrate, fluvastatin, gemfibrozil, ispaghula, nictotinic acid, omega-3 triglycerides, pravastatin, rosuvastatin and simvastatin.

35) Drugs for cystic fibrosis management such as, for example, *Pseudomonas aeruginosa* infection vaccines (eg Aerugen™), alpha 1-antitripsin, amikacin, cefadroxil, denufosol, duramycin, glutathione, mannitol, and tobramycin.

36) Diagnostic agents such as, for example, adenosine and aminohippuric acid.

37) Dietary supplements such as, for example, melatonin and vitamins including vitamin E.

38) Diuretics such as, for example, amiloride, bendroflumethiazide, bumetanide, chlortalidone, cyclopenthiazide, furosemide, indapamide, metolazone, spironolactone and torasemide.

39) Dopamine agonists such as, for example, amantadine, apomorphine, bromocriptine, cabergoline, lisuride, pergolide, pramipexole and ropinerole.

40) Drugs for treating erectile dysfunction, such as, for example, apomorphine, apomorphine diacetate, moxisylyte, phentolamine, phosphodiesterase type 5 inhibitors, such as sildenafil, tadalafil, vardenafil and yohimbine.

41) Gastrointestinal agents such as, for example, atropine, hyoscyamine, famotidine, lansoprazole, loperamide, omeprazole and rebeprazole.

42) Hormones and analogues such as, for example, cortisone, epinephrine, estradiol, insulin, Ostabolin-C, parathyroid hormone and testosterone.

43) Hormonal drugs such as, for example, desmopressin, lanreotide, leuprolide, octreotide, pegvisomant, protirelin, salcotonin, somatropin, tetracosactide, thyroxine and vasopressin.

44) Hypoglycaemics such as, for example, sulphonylureas including glibenclamide, gliclazide, glimepiride, glipizide and gliquidone; biguanides including metformin; thiazolidinediones including pioglitazone, rosiglitazone, nateglinide, repaglinide and acarbose.

45) Immunoglobulins.

46) Immunomodulators such as, for example, interferon (e.g. interferon beta-1a and interferon beta-1b) and glatiramer.

47) Immunosupressives such as, for example, azathioprine, cyclosporin, mycophenolic acid, rapamycin, sirolimus and tacrolimus.

48) Mast cell stabilizers such as, for example, cromoglycate, iodoxamide, nedocromil, ketotifen, tryptase inhibitors and pemirolast.

49) Drugs for treatment of migraine headaches such as, for example, almotriptan, alperopride, amitriptyline, amoxapine, atenolol, clonidine, codeine, coproxamol, cyproheptadine, dextropropoxypene, dihydroergotamine, diltiazem, doxepin, ergotamine, eletriptan, fluoxetine, frovatriptan, isometheptene, lidocaine, lisinopril, lisuride, loxapine, methysergide, metoclopramide, metoprolol, nadolol, naratriptan, nortriptyline, oxycodone, paroxetine, pizotifen, pizotyline, prochlorperazine propanolol, propoxyphene, protriptyline, rizatriptan, sertraline, sumatriptan, timolol, tolfenamic acid, tramadol, verapamil, zolmitriptan, and non-steroidal anti-inflammatory drugs.

50) Drugs for treatment of motion sickness such as, for example, diphenhydramine, promethazine and scopolamine.

51) Mucolytic agents such as N-acetylcysteine, ambroxol, amiloride, dextrans, heparin, desulphated heparin, low molecular weight heparin and recombinant human DNase.

52) Drugs for multiple sclerosis management such as, for example, bencyclane, methylprednisolone, mitoxantrone and prednisolone.

53) Muscle relaxants such as, for example, baclofen, chlorzoxazone, cyclobenzaprine, methocarbamol, orphenadrine, quinine and tizanidine.

54) NMDA receptor antagonists such as, for example, mementine.

55) Nonsteroidal anti-inflammatory agents such as, for example, aceclofenac, acetaminophen, alminoprofen, amfenac, aminopropylon, amixetrine, aspirin, benoxaprofen, bromfenac, bufexamac, carprofen, celecoxib, choline, cinchophen, cinmetacin, clometacin, clopriac, diclofenac, diclofenac sodium, diflunisal, ethenzamide, etodolac, etoricoxib, fenoprofen, flurbiprofen, ibuprofen, indomethacin, indoprofen, ketoprofen, ketorolac, loxoprofen, mazipredone, meclofenamate, mefenamic acid, meloxicam, nabumetone, naproxen, nimesulide, parecoxib, phenylbutazone, piroxicam, pirprofen, rofecoxib, salicylate, sulindac, tiaprofenic acid, tolfenamate, tolmetin and valdecoxib.

56) Nucleic-acid medicines such as, for example, oligonucleotides, decoy nucleotides, antisense nucleotides and other gene-based medicine molecules.

57) Opiates and opioids such as, for example, alfentanil, allylprodine, alphaprodine, anileridine, benzylmorphine, bezitramide, buprenorphine, butorphanol, carbiphene, cipramadol, clonitazene, codeine, codeine phosphate, dextromoramide, dextropropoxyphene, diamorphine, dihydrocodeine, dihydromorphine, diphenoxylate, dipipanone, fentanyl, hydromorphone, L-alpha acetyl methadol, levorphanol, lofentanil, loperamide, meperidine, meptazinol, methadone, metopon, morphine, nalbuphine, nalorphine, oxycodone, papaveretum, pentazocine, pethidine, phenazocine, pholcodeine, remifentanil, sufentanil, tramadol, and combinations thereof with an anti-emetic.

58) Opthalmic preparations such as, for example, betaxolol and ketotifen.

59) Osteoporosis preparations such as, for example, alendronate, estradiol, estropitate, raloxifene and risedronate.

60) Other analgesics such as, for example, apazone, benzpiperylon, benzydamine, caffeine, cannabinoids, clonixin, ethoheptazine, flupirtine, nefopam, orphenadrine, pentazocine, propacetamol and propoxyphene.

61) Other anti-inflammatory agents such as, for example, B-cell inhibitors, p38 MAP kinase inhibitors and TNF inhibitors.

62) Phosphodiesterase inhibitors such as, for example, nonspecific phosphodiesterase inhibitors including theophylline, theobromine, IBMX, pentoxifylline and papaverine; phosphodiesterase type 3 inhibitors including bipyridines such as milrinone, amrinone and olprinone; imidazolones such as piroximone and enoximone; imidazolines such as imazodan and 5-methyl-imazodan; imidazo-quinoxalines; and dihydropyridazinones such as indolidan and LY181512 (5-(6-oxo-1,4,5,6-tetrahydro-pyridazin-3-yl)-1,3-dihydro-indol-2-one); dihydroquinolinone compounds such as cilostamide, cilostazol, and vesnarinone; motapizone; phosphodiesterase type 4 inhibitors such as cilomilast, etazolate, rolipram, oglemilast, roflumilast, ONO 6126, tolafentrine and zardaverine, and including quinazolinediones such as nitraquazone and nitraquazone analogs; xanthine derivatives such as denbufylline and arofylline; tetrahydropyrimidones such as atizoram; and oxime carbamates such as filaminast; and phosphodiesterase type 5 inhibitors including sildenafil, zaprinast, vardenafil, tadalafil, dipyridamole, and the compounds described in WO 01/19802, particularly (S)-2-(2-hydroxymethyl-1-pyrrolidinyl)-4-(3-chloro-4-methoxy-benzylamino)-5-[N-(2-pyrimidinylmethyl)carbamoyl]pyrimidine, 2-(5,6,7,8-tetrahydro-1,7-naphthyridin-7-y1)-4-(3-chloro-4-methoxybenzylamino)-5-[N-(2-morpholinoethyl) carbamoyl]-pyrimidine, and (S)-2-(2-hydroxymethyl-1-pyrrolidinyl)-4-(3-chloro-4-methoxy-benzylamino)-5-[N-(1,3,5-trimethyl-4-pyrazolyl)carbamoyl]-pyrimidine).

63) Potassium channel modulators such as, for example, cromakalim, diazoxide, glibenclamide, levcromakalim, minoxidil, nicorandil and pinacidil.

64) Prostaglandins such as, for example, alprostadil, dinoprostone, epoprostanol and misoprostol.

65) Respiratory agents and agents for the treatment of respiratory diseases including bronchodilators such as, for example, the $\beta_2$-agonists bambuterol, bitolterol, broxaterol, carmoterol, clenbuterol, fenoterol, formoterol, indacaterol, levalbuterol, metaproterenol, orciprenaline, picumeterol, pirbuterol, procaterol, reproterol, rimiterol, salbutamol, salmeterol, terbutaline and the like; inducible nitric oxide synthase (iNOS) inhibitors; the antimuscarinics ipratropium, ipratropium bromide, oxitropium, tiotropium, glycopyrrolate and the like; the xanthines aminophylline, theophylline and the like; adenosine receptor antagonists, cytokines such as, for example, interleukins and interferons; cytokine antagonists and chemokine antagonists including cytokine synthesis inhibitors, endothelin receptor antagonists, elastase inhibitors, integrin inhibitors, leukotrine receptor antagonists, prostacyclin analogues, and ablukast, ephedrine, epinephrine, fenleuton, iloprost, iralukast, isoetharine, isoproterenol, montelukast, ontazolast, pranlukast, pseudoephedrine, sibenadet, tepoxalin, verlukast, zafirlukast and zileuton.

66) Sedatives and hypnotics such as, for example, alprazolam, butalbital, chlordiazepoxide, diazepam, estazolam, flunitrazepam, flurazepam, lorazepam, midazolam, temazepam, triazolam, zaleplon, zolpidem, and zopiclone.

67) Serotonin agonists such as, for example, 1-(4-bromo-2,5-dimethoxyphenyl)-2-aminopropane, buspirone, m-chlorophenylpiperazine, cisapride, ergot alkaloids, gepirone, 8-hydroxy-(2-N,N-dipropylamino)-tetraline, ipsaperone, lysergic acid diethylamide, 2-methyl serotonin, mezacopride, sumatriptan, tiaspirone, trazodone and zacopride.

68) Serotonin antagonists such as, for example, amitryptiline, azatadine, chlorpromazine, clozapine, cyproheptadine, dexfenfluramine, R(+)-α-(2,3-dimethoxyphenyl)-1-[2-(4-fluorophenyl)ethyl]-4-piperidine-methanol, dolasetron, fenclonine, fenfluramine, granisetron, ketanserin, methysergide, metoclopramide, mianserin, ondansetron, risperidone, ritanserin, trimethobenzamide and tropisetron.

69) Steroid drugs such as, for example, alcometasone, beclomethasone, beclomethasone dipropionate, betamethasone, budesonide, butixocort, ciclesonide, clobetasol, deflazacort, diflucortolone, desoxymethasone, dexamethasone, fludrocortisone, flunisolide, fluocinolone, fluometholone, fluticasone, fluticasone proprionate, hydrocortisone, methylprednisolone, mometasone, nandrolone decanoate, neomycin sulphate, prednisolone, rimexolone, rofleponide, triamcinolone and triamcinolone acetonide.

70) Sympathomimetic drugs such as, for example, adrenaline, dexamfetamine, dipirefin, dobutamine, dopamine, dopexamine, isoprenaline, noradrenaline, phenylephrine, pseudoephedrine, tramazoline and xylometazoline.

71) Nitrates such as, for example, glyceryl trinitrate, isosorbide dinitrate and isosorbide mononitrate.

72) Skin and mucous membrane agents such as, for example, bergapten, isotretinoin and methoxsalen.

73) Smoking cessation aids such as, for example, bupropion, nicotine and varenicline.

74) Drugs for treatment of Tourette's syndrome such as, for example, pimozide.

75) Drugs for treatment of urinary tract infections such as, for example, darifenicin, oxybutynin, propantheline bromide and tolteridine.

76) Vaccines.

77) Drugs for treating vertigo such as, for example, betahistine and meclizine.

78) Therapeutic proteins and peptides such as acylated insulin, glucagon, glucagon-like peptides, exendins, insulin, insulin analogues, insulin aspart, insulin detemir, insulin glargine, insulin glulisine, insulin lispro, insulin zinc, isophane insulins, neutral, regular and insoluble insulins, and protamine zinc insulin.

79) Anticancer agents such as, for example, anthracyclines, doxorubicin, idarubicin, epirubicin, methotrexate, taxanes, paclitaxel, docetaxel, cisplatin, vinca alkaloids, vincristine and 5-fluorouracil.

80) Pharmaceutically acceptable salts or derivatives of any of the foregoing.

It should be noted that drugs listed above under a particular indication or class may also find utility in other indications. A plurality of active agents can be employed in the practice of the present invention. An inhaler according to the invention may also be used to deliver combinations of two or more different active agents or drugs. Specific combinations of two medicaments which may be mentioned include combinations of steroids and $\beta_2$-agonists. Examples of such combinations are beclomethasone and formoterol; beclomethasone and salmeterol; fluticasone and formoterol; fluticasone and salmeterol; budesonide and formoterol; budesonide and salmeterol; flunisolide and formoterol; flunisolide and salmeterol; ciclesonide and formoterol; ciclesonide and salmeterol; mometasone and formoterol; and mometasone and salmeterol. Specifically, inhalers according to the invention may also be used to deliver combinations of three different active agents or drugs.

It will be clear to a person of skill in the art that, where appropriate, the active agents or drugs may be linked to a carrier molecule or molecules and/or used in the form of prodrugs, salts, as esters, or as solvates to optimise the activity and/or stability of the active agent or drug.

Anticholinergic agents are referred to above (see No. 15). It is also envisaged that the pharmaceutical composition may comprise one or more, preferably one, anticholinergic 1, optionally in combination with a pharmaceutically acceptable excipient.

The anticholinergic 1 can be selected from the group consisting of a) tiotropium salts 1a, b) compounds of formula 1c

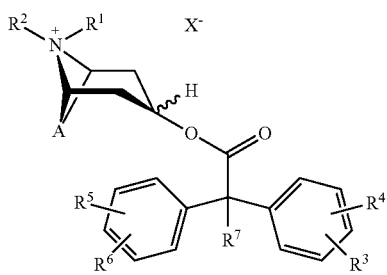

wherein

A denotes a double-bonded group selected from among

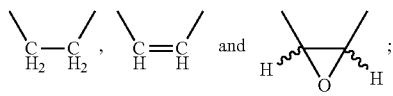

$X^-$ denotes an anion with a single negative charge, preferably an anion selected from the group consisting of fluoride, chloride, bromide, iodide, sulphate, phosphate, methanesulphonate, nitrate, maleate, acetate, citrate, fumarate, tartrate, oxalate, succinate, benzoate and p-toluenesulphonate, $R^1$ and $R^2$ which may be identical or different denote a group selected from among methyl, ethyl, n-propyl and iso-propyl, which may optionally be substituted by hydroxy or fluorine, preferably unsubstituted methyl;

$R^3$, $R^4$, $R^5$ and $R^6$, which may be identical or different, denote hydrogen, methyl, ethyl, methyloxy, ethyloxy, hydroxy, fluorine, chlorine, bromine, CN, $CF_3$ or $NO_2$;

$R^7$ denotes hydrogen, methyl, ethyl, methyloxy, ethyloxy, —$CH_2$—F, —$CH_2$—$CH_2$—F, -0-$CH_2$—F, -0-$CH_2$—$CH_2$—F, —$CH_2$—OH, —$CH_2$—$CH_2$—OH, $CF_3$, —$CH_2$—OMe, —$CH_2$—$CH_2$—OMe, —$CH_2$—OEt, —$CH_2$—$CH_2$—OEt, —O—COMe, —O—COEt, -Q-$COCF_3$, -Q-$COCF_3$, fluorine, chlorine or bromine;

c) compounds of formula 1d

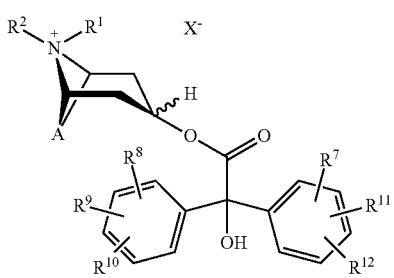

wherein

A, $X^-$, $R^1$ and $R^2$ may have the meanings as mentioned hereinbefore and wherein $R^7$, $R^8$, $R^9$, $R^{10}$, $R^{11}$ and $R^{12}$, which may be identical or different, denote hydrogen, methyl, ethyl, methyloxy, ethyloxy, hydroxy, fluorine, chlorine, bromine, CN, $CF_3$ or $NO_2$, with the proviso that at least one of the groups $R^7$, $R^8$, $R^9$, $R^{10}$, $R^{11}$ and $R^{12}$ is not hydrogen, d) compounds of formula 1e

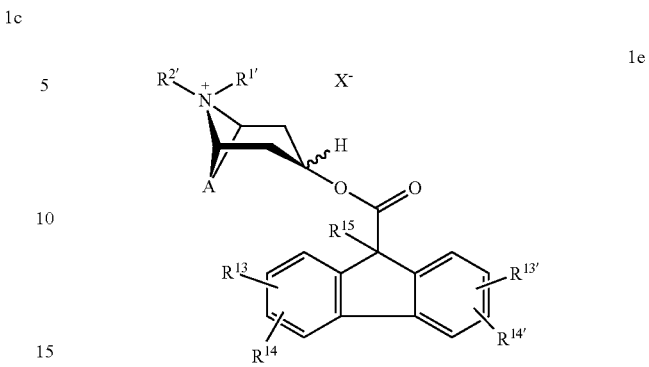

wherein A and $X^-$ may have the meanings as mentioned hereinbefore, and wherein $R^{15}$ denotes hydrogen, hydroxy, methyl, ethyl, —$CF_3$, $CHF_2$ or fluorine;

$R^{1'}$ and $R^{2'}$ which may be identical or different denote $C_1$-$C_5$-alkyl which may optionally be substituted by $C_3$-$C_6$-cycloalkyl, hydroxy or halogen, or $R^{1'}$ and $R2'$ together denote a —$C_3$-$C_5$-alkylene-bridge;

$R^{13}$, $R^{14}$, $R^{13'}$ and $R^{14'}$ which may be identical or different denote hydrogen, —$C_1$-$C_4$-alkyl, —$C_1$-$C_4$-alkyloxy, hydroxy, —$CF_3$, —$CHF_2$, CN, $NO_2$ or halogen, e) compounds of formula 1f

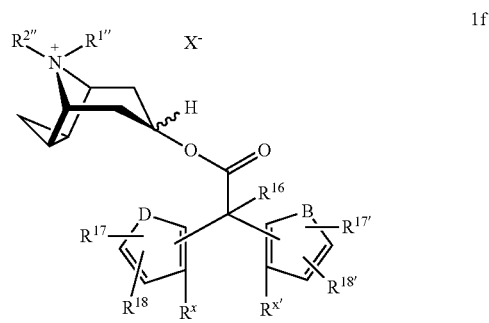

wherein $X^-$ may have the meanings as mentioned hereinbefore, and wherein

D and B which may be identical or different, preferably identical, denote —O—, —S—, —NH—, —$CH_2$—, —CH═CH—, or —N($C_1$-$C_4$-alkyl)-;

$R^{16}$ denotes hydrogen, hydroxy, —$C_1$-$C_4$-alkyl, —$C_1$-$C_4$-alkyloxy, —$C_1$-$C_4$-alkylene-Halogen, —O—$C_1$-$C_4$ alkylene-halogen, —$C_1$-$C_4$-alkylene-OH, —$CF_3$, $CHF_2$, —$C_1$-$C_4$-alkylene-$C_1$-$C_4$ alkyloxy, —O—$COC_1$-$C_4$-alkyl, —O—$COC_1$-$C_4$-alkylene-halogen, —$C_1$-$C_4$-alkylene-$C_3$-$C_6$-cycloalkyl, —O—$COCF_3$ or halogen;

$R^{1'''}$ and $R^{2''}$ which may be identical or different, denote —$C_1$-$C_5$-alkyl, which may optionally be substituted by —$C_3$-$C_6$-cycloalkyl, hydroxy or halogen, or $R^{1'''}$ and $R^{2''}$ together denote a —$C_3$-$C_5$-alkylene bridge;

$R^{17}$, $R^{18}$, $R^{17'}$ and $R^{18'}$, which may be identical or different, denote hydrogen, $C_1$-$C_4$-alkyl, $C_1$-$C_4$-alkyloxy, hydroxy, —$CF_3$, CN, $NO_2$ or halogen;

$R^x$ and $R^{x'}$ which may be identical or different, denote hydrogen, $C_1$-$C_4$-alkyl, $C_1$-$C_4$-alkyloxy, hydroxy, —$CF_3$, CN, $NO_2$ or halogen or $R^x$ and $R^{x'}$ together denote a single bond or a bridging group selected from among the bridges —O—, —S—, —NH—, —$CH_2$—, —$CH_2$—$CH_2$—, —N($C_1$-$C_4$-alkyl), —CH($C_1$-$C_4$-alkyl)- and —C($C_1$-$C_4$-alkyl)$_2$, and f) compounds of formula 1g

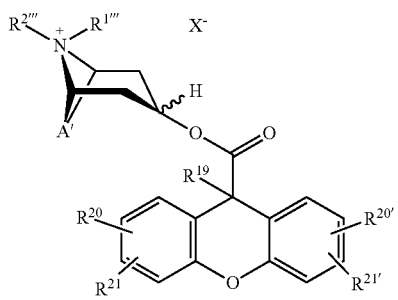

wherein $X^-$ may have the meanings as mentioned hereinbefore, and wherein A' denotes a double-bonded group selected from among

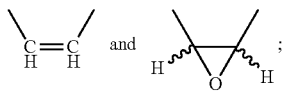

$R^{19}$ denotes hydroxy, methyl, hydroxymethyl, ethyl, —$CF_3$, $CHF_2$ or fluorine;
$R^{1'''}$ and $R^{2'''}$ which may be identical or different denote $C_1$-$C_5$-alkyl which may optionally be substituted by $C_3$-$C_6$-cycloalkyl, hydroxy or halogen, or
$R^{1'''}$ and $R^{2'''}$ together denote a —$C_3$-$C_5$-alkylene-bridge;
$R^{20}$, $R^{21}$, $R^{20'}$ and $R^{21'}$ which may be identical or different denote hydrogen, —$C_1$-$C_4$-alkyl, —$C_1$-$C_4$-alkyloxy, hydroxy, —$CF_3$, —$CHF_2$, CN, $NO_2$ or halogen.

The compounds of formula 1c are known in the art (WO 02/32899).

In a preferred embodiment of the invention the method comprises administration of compounds of formula 1c, wherein
$X^-$ denotes bromide;
$R^1$ and $R^2$ which may be identical or different denote a group selected from methyl and ethyl, preferably methyl;
$R^3$, $R^4$, $R^5$ and $R^6$, which may be identical or different, denote hydrogen, methyl, methyloxy, chlorine or fluorine;
$R^7$ denotes hydrogen, methyl or fluorine, optionally together with a pharmaceutically acceptable excipient.

Of particular importance are compounds of general formula 1c, wherein A denotes a double-bonded group selected from among

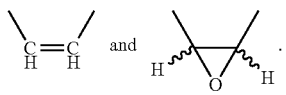

The compounds of formula 1c, may optionally be administered in the form of the individual optical isomers, mixtures of the individual enantiomers or racemates thereof.

Of particular importance within a method according to the invention are the following compounds of formula 1c:
tropenol 2,2-diphenylpropionic acid ester methobromide,
scopine 2,2-diphenylpropionic acid ester methobromide,
scopine 2-fluoro-2,2-diphenylacetic acid ester methobromide and
tropenol 2-fluoro-2,2-diphenylacetic acid ester methobromide.

The compounds of formula 1d are known in the art (WO 02/32898).

In a preferred embodiment of the invention the method comprises administration of compounds of formula 1d, wherein
A denotes a double-bonded group selected from among

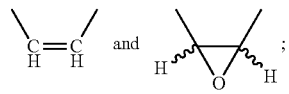

$X^-$ denotes bromide;
$R^1$ and $R^2$ which may be identical or different denote methyl or ethyl, preferably methyl;
$R^7$, $R^8$, $R^9$, $R^{10}$, $R^{11}$ and $R^{12}$, which may be identical or different, denote hydrogen, fluorine, chlorine or bromine, preferably fluorine with the proviso that at least one of the groups $R^7$, $R^8$, $R^9$, $R^{10}$, $R^{11}$ and $R^{12}$ not hydrogen, optionally together with a pharmaceutically acceptable excipient.

Of particular importance within the method according to the invention are the following compounds of formula 1d:
tropenol 3,3',4,4'-tetrafluorobenzilic acid ester methobromide,
scopine 3,3',4,4'-tetrafluorobenzilic acid ester methobromide,
scopine 4,4'-difluorobenzilic acid ester methobromide,
tropenol 4,4'-difluorobenzilic acid ester methobromide,
scopine 3,3'-difluorobenzilic acid ester methobromide, and
tropenol 3,3'-difluorobenzilic acid ester methobromide.

The pharmaceutical compositions according to the invention may contain the compounds of formula 1d optionally in the form of the individual optical isomers, mixtures of the individual enantiomers or racemates thereof.

The compounds of formula 1e are known in the art (WO 03/064419).

In a preferred embodiment of the invention the method comprises administration of compounds of formula 1e, wherein
A denotes a double-bonded group selected from among

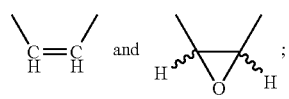

$X^-$ denotes an anion selected from among chloride, bromide and methanesulphonate, preferably bromide;
$R^{15}$ denotes hydroxy, methyl or fluorine, preferably methyl or hydroxy;
$R^{1'}$ and $R^{2'}$ which may be identical or different represent methyl or ethyl, preferably methyl;
$R^{13}$, $R^{14}$, $R^{13'}$ and $R^{14'}$ which may be identical or different represent hydrogen, —$CF_3$, —$CHF_2$ or fluorine, preferably hydrogen or fluorine, optionally together with a pharmaceutically acceptable excipient.

In another preferred embodiment of the invention the method comprises administration of compounds of formula 1e, wherein A denotes a double-bonded group selected from among

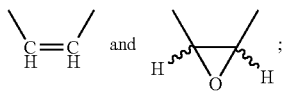

X⁻ denotes bromide;
$R^{15}$ denotes hydroxy or methyl, preferably methyl;
$R^{1'}$ and $R^{2'}$ which may be identical or different represent methyl or ethyl, preferably methyl;
$R^{13}$, $R^{14}$, $R^{13'}$ and $R^{14'}$ which may be identical or different represent hydrogen or fluorine, optionally together with a pharmaceutically acceptable excipient.

Of particular importance within the method according to the invention are the following compounds of formula 1e:
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide.

The pharmaceutical compositions according to the invention may contain the compounds of formula 1e optionally in the form of the individual optical isomers, mixtures of the individual enantiomers or racemates thereof.

The compounds of formula 1f are known in the art (WO 03/064418).

In another preferred embodiment of the invention the method comprises administration of compounds of formula 1f wherein
X⁻ denotes chloride, bromide, or methanesulphonate, preferably bromide;
D and B which may be identical or different, preferably identical, denote —O—, —S—, —NH or —CH═CH—;
$R^{16}$ denotes hydrogen, hydroxy, —$C_1$-$C_4$-alkyl, —$C_1$-$C_4$ alkyloxy, —$CF_3$, —$CHF_2$, fluorine, chlorine or bromine;
$R^{1''}$ and $R^{2''}$ which may be identical or different, denote $C_1$-$C_4$-alky, which may optionally be substituted by hydroxy, fluorine, chlorine or bromine, or
$R^{1''}$ and $R^{2''}$ together denote a —$C_3$-$C_4$-alkylene-bridge;
$R^{17}$, $R^{18}$, $R^{17'}$ and $R^{18'}$, which may be identical or different, denote hydrogen, $C_1$-$C_4$-alkyl, $C_1$-$C_4$-alkyloxy, hydroxy, —$CF_3$, —$CHF_2$, CN, $NO_2$, fluorine, chlorine or bromine;
$R^x$ and $R^{x'}$ which may be identical or different, denote hydrogen, $C_1$-$C_4$-alkyl, $C_1$-$C_4$-alkyloxy, hydroxy, —$CF_3$, —$CHF_2$, CN, $NO_2$, fluorine, chlorine or bromine or
$R^x$ and $R^{x'}$ together denote a single bond or a bridging group selected from among the bridges —O—, —S—, —NH— and —$CH_2$—, optionally together with a pharmaceutically acceptable excipient.

In another preferred embodiment of the invention the method comprises administration of compounds of formula 1f, wherein
X⁻ denotes chloride, bromide, or methanesulphonate, preferably bromide;
D and B which may be identical or different, preferably identical, denote —S or —CH═CH—;
$R^{16}$ denotes hydrogen, hydroxy or methyl;
$R^{1''}$ and $R^{2''}$ which may be identical or different, denote methyl or ethyl;
$R^{17}$, $R^{18}$, $R^{17'}$ and $R^{18'}$, which may be identical or different, denote hydrogen, —$CF_3$ or fluorine, preferably hydrogen;
$R^x$ and $R^{x'}$ which may be identical or different, denote hydrogen, —$CF_3$ or fluorine, preferably hydrogen or $R^x$ and $R^{x'}$ together denote a single bond or the bridging group —O—, optionally together with a pharmaceutically acceptable excipient.

In another preferred embodiment of the invention the method comprises administration of compounds of formula 1f wherein
X⁻ denotes bromide;
D and B denote —CH═CH—;
$R^{16}$ denotes hydrogen, hydroxy or methyl;
$R^{1''}$ and $R^{2''}$ denote methyl;
$R^{17}$, $R^{18}$, $R^{17'}$ and $R^{18'}$, which may be identical or different, denote hydrogen or fluorine, preferably hydrogen;
$R^x$ and $R^{x'}$ which may be identical or different, denote hydrogen or fluorine, preferably hydrogen or
$R^x$ and $R^{x'}$ together denote a single bond or the bridging group —O—, optionally together with a pharmaceutically acceptable excipient.

Of particular importance within the method according to the invention are the following compounds of formula 1f:
cyclopropyltropine benzilate methobromide;
cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide; cyclopropyltropine 9-methyl-xanthene-9-carboxylate methobromide; cyclopropyltropine 9-hydroxy-fluorene-9-carboxylate methobromide; cyclopropyltropine methyl 4,4'-difluorobenzilate methobromide.

The pharmaceutical compositions according to the invention may contain the compounds of formula 1f optionally in the form of the individual optical isomers, mixtures of the individual enantiomers or racemates thereof.

The compounds of formula 1g are known in the art (WO 03/064417).

In another preferred embodiment of the invention the method comprises administration of compounds of formula 1g wherein
A' denotes a double-bonded group selected from among

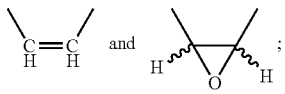

X⁻ denotes chloride, bromide or methanesulphonate, preferably bromide;
$R^{19}$ denotes hydroxy or methyl;
$R^{1'''}$ and $R^{2'''}$ which may be identical or different represent methyl or ethyl, preferably methyl;
$R^{20}$, $R^{21}$, $R^{20'}$ and $R^{21'}$ which may be identical or different represent hydrogen, —$CF_3$, —$CHF_2$ or fluorine, preferably hydrogen or fluorine, optionally together with a pharmaceutically acceptable excipient.

In another preferred embodiment of the invention the method comprises administration of compounds of formula 1g wherein
A' denotes a double-bonded group selected from among

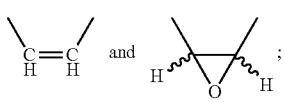

X⁻ denotes bromide;
R¹⁹ denotes hydroxy or methyl, preferably methyl;
R¹‴ and R²‴ which may be identical or different represent methyl or ethyl, preferably methyl;
R³, R⁴, R³' and R⁴' which may be identical or different represent hydrogen or fluorine, optionally together with a pharmaceutically acceptable excipient.

Of particular importance within the method according to the invention are the following compounds of formula 1g:
tropenol 9-hydroxy-xanthene-9-carboxylate methobromide;
scopine 9-hydroxy-xanthene-9-carboxylate methobromide;
tropenol 9-methyl-xanthene-9-carboxylate methobromide;
scopine 9-methyl-xanthene-9-carboxylate methobromide;
tropenol 9-ethyl-xanthene-9-carboxylate methobromide;
tropenol 9-difluoromethyl-xanthene-9-carboxylate methobromide;
scopine 9-hydroxymethyl-xanthene-9-carboxylate methobromide.

The pharmaceutical compositions according to the invention may contain the compounds of formula 1g optionally in the form of the individual optical isomers, mixtures of the individual enantiomers or racemates thereof.

The alkyl groups used, unless otherwise stated, are branched and unbranched alkyl groups having 1 to 5 carbon atoms. Examples include: methyl, ethyl, propyl or butyl. The groups methyl, ethyl, propyl or butyl may optionally also be referred to by the abbreviations Me, Et, Prop or Bu. Unless otherwise stated, the definitions propyl and butyl also include all possible isomeric forms of the groups in question. Thus, for example, propyl includes n-propyl and iso-propyl, butyl includes iso-butyl, sec. butyl and tert.-butyl, etc.

The cycloalkyl groups used, unless otherwise stated, are alicyclic groups with 3 to 6 carbon atoms. These are the cyclopropyl, cyclobutyl, cyclopentyl and cyclohexyl groups. According to the invention cyclopropyl is of particular importance within the scope of the present invention.

The alkylene groups used, unless otherwise stated, are branched and unbranched double-bonded alkyl bridges with 1 to 5 carbon atoms. Examples include: methylene, ethylene, propylene or butylene.

The alkylene-halogen groups used, unless otherwise stated, are branched and unbranched double-bonded alkyl bridges with 1 to 4 carbon atoms which may be mono-, di- or trisubstituted, preferably disubstituted, by a halogen. Accordingly, unless otherwise stated, the term alkylene-OH groups denotes branched and unbranched double-bonded alkyl bridges with 1 to 4 carbon atoms which may be mono-, di- or trisubstituted, preferably monosubstituted, by a hydroxy.

The alkyloxy groups used, unless otherwise stated, are branched and unbranched alkyl groups with 1 to 5 carbon atoms which are linked via an oxygen atom. The following may be mentioned, for example: methyloxy, ethyloxy, propyloxy or butyloxy. The groups methyloxy, ethyloxy, propyloxy or butyloxy may optionally also be referred to by the abbreviations MeO, EtO, PropO or BuO. Unless otherwise stated, the definitions propyloxy and butyloxy also include all possible isomeric forms of the groups in question. Thus, for example, propyloxy includes n-propyloxy and iso-propyloxy, butyloxy includes iso-butyloxy, sec. butyloxy and tert.-butyloxy, etc. The word alkoxy may also possibly be used within the scope of the present invention instead of the word alkyloxy. The groups methyloxy, ethyloxy, propyloxy or butyloxy may optionally also be referred to as methoxy, ethoxy, propoxy or butoxy.

The alkylene-alkyloxy groups used, unless otherwise stated, are branched and unbranched double-bonded alkyl bridges with 1 to 5 carbon atoms which may be mono-, di- or trisubstituted, preferably monosubstituted, by an alkyloxy group.

The —O—CO-alkyl groups used, unless otherwise stated, are branched and unbranched alkyl groups with 1 to 4 carbon atoms which are bonded via an ester group. The alkyl groups are bonded directly to the carbonylcarbon of the ester group. The term —O—CO-alkyl-halogen group should be understood analogously. The group —O—CO—CF₃ denotes trifluoroacetate.

Within the scope of the present invention halogen denotes fluorine, chlorine, bromine or iodine. Unless otherwise stated, fluorine and bromine are the preferred halogens. The group CO denotes a carbonyl group.

The inhalation device according to the invention comprises the compounds of formula 1 preferably in admixture with a pharmaceutically acceptable excipient to form a powder mixture. The following pharmaceutically acceptable excipients may be used to prepare these inhalable powder mixtures according to the invention: monosaccharides (e.g. glucose or arabinose), disaccharides (e.g. lactose, saccharose, maltose, trehalose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose and trehalose are the particularly preferred excipients, while lactose, preferably in form of its monohydrate is most particularly preferred.

The compounds of formula 1 may be used in the form of their racemates, enantiomers or mixtures thereof. The separation of enantiomers from the racemates may be carried out using methods known in the art (e.g. by chromatography on chiral phases, etc.).

Optionally, the inhalation device according to the invention contains plural of doses of a medicament in powder form that contains, beside one compound of formula 1, another active ingredient.

Preferably the additional active ingredient is a beta₂ agonists 2 which is selected from the group consisting of albuterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmeterol, salmefamol, soterenot, sulphonterol, tiaramide, terbutaline, tolubuterol, CHF-1035, HOKU-81, KUL-1248, 3-(4-{6-[2-Hydroxy-2-(4-hydroxy-3-hydroxymethyl-phenyl)-ethylamino]-hexyloxy}-butyl)-benzenesulfoneamide, 5-[2-(5,6-Diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-0X0-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluormethylphenyl)-2- tert.-butylamino)ethanol and 1-(4-ethoxycarbonylamino-3-cyano-5-fluorophenyl)-2-(tert.-butylamino)ethanol,
optionally in the form of the racemates, the enantiomers, the diastereomers and optionally the pharmacologically acceptable acid addition salts and the hydrates thereof.

According to the instant invention more preferred beta$_2$ agonists 2 are selected from the group consisting of bambuterol, bitolterol, carbuterol, clenbuterol, fenoterol, formoterol, hexoprenaline, ibuterol, pirbuterol, procaterol, reproterol, salmeterol, sulphonterol, terbutaline, tolubuterol, 3-(4-{6-[2-Hydroxy-2-(4-hydroxy-3-hydroxymethyl-phenyl)-ethylamino]-hexyloxy}-butyl)-benzenesulfoneamide, 5-[2-(5,6-Diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-0X0-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluormethylphenyl)-2-tert.-butylamino)ethanol and 1-(4-ethoxycarbonylamino-3-cyano-5-fluorophenyl)-2-(tert.-butylamino)ethanol, optionally in the form of the racemates, the enantiomers, the diastereomers and optionally the pharmacologically acceptable acid addition salts and the hydrates thereof.

More preferably, the betamimetics 2 used as within the compositions according to the invention are selected from among fenoterol, formoterol, salmeterol, 3-(4-{6-[2-Hydroxy-2-(4-hydroxy-3-hydroxymethyl-phenyl)-ethylamino]-hexyloxy}-butyl)-benzenesulfoneamide, 5-[2-(5,6-Diethyl-indan-2-ylamino)-1-hydroxy-ethyl]-8-hydroxy-1H-quinolin-2-one, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, optionally in the form of the racemates, the enantiomers, the diastereomers and optionally the pharmacologically acceptable acid addition salts thereof, and the hydrates thereof. Of the betamimetics mentioned above the compounds formoterol, salmeterol, 3-(4-{6-[2-Hydroxy-2-(4-hydroxy-3-hydroxymethyl-phenyl)-ethylamino]-hexyloxy}-butyl)benzenesulfoneamide, and 5-[2-(5,6-Diethyl-indan-2-ylamino)-1-hydroxy-ethyl]-8-hydroxy-1H-quinolin-2-one are particularly preferred, optionally in the form of the racemates, the enantiomers, the diastereomers and optionally the pharmacologically acceptable acid addition salts thereof, and the hydrates thereof. Of the betamimetics mentioned above the compounds formoterol and salmeterol are particularly preferred, optionally in the form of the racemates, the enantiomers, the diastereomers and optionally the pharmacologically acceptable acid addition salts thereof, and the hydrates thereof.

Examples of pharmacologically acceptable acid addition salts of the betamimetics 2 according to the invention are the pharmaceutically acceptable salts which are selected from among the salts of hydrochloric acid, hydrobromic acid, sulphuric acid, phosphoric acid, methanesulphonic acid, acetic acid, fumaric acid, succinic acid, lactic acid, citric acid, tartaric acid, 1-hydroxy-2-naphthalenecarboxylic acid, 4-phenylcinnamic acid, 5-(2,4-difluorophenyl)salicylic acid or maleic acid. If desired, mixtures of the abovementioned acids may also be used to prepare the salts 2.

According to the invention, the salts of the betamimetics 2 selected from among the hydrochloride, hydrobromide, sulphate, phosphate, fumarate, methanesulphonate, 4-phenylcinnamate, 5-(2,4-difluorophenyl)salicylate, maleate and xinafoate are preferred. Particularly preferred are the salts of 2 in the case of salmeterol selected from among the hydrochloride, sulphate, 4-phenylcinnamate, 5-(2,4-difluorophenyl)salicylate and xinafoate, of which the 4-phenylcinnamate, 5-(2,4-difluorophenyl)salicylate and especially xinafoate are particularly important. Particularly preferred are the salts of 2 in the case of formoterol selected from the hydrochloride, sulphate and fumarate, of which the hydrochloride and fumarate are particularly preferred, such as formoterol fumarate.

Salts of salmeterol, formoterol, 3-(4-{6-[2-Hydroxy-2-(4-hydroxy-3-hydroxymethyl-phenyl)-ethylamino]-hexyloxy}-butyl)-benzenesulfoneamide, and 5-[2-(5,6-Diethyl-indan-2-ylamino)-1-hydroxy-ethyl]-8-hydroxy-1H-quinolin-2-one, are preferably used as the betamimetics 2 according to the invention. Of particular importance are salmeterol and formoterol salts. Any reference to the term betamimetics 2 also includes a reference to the relevant enantiomers or mixtures thereof. In the pharmaceutical compositions according to the invention, the compounds 2 may be present in the form of their racemates, enantiomers or mixtures thereof. The separation of the enantiomers from the racemates may be carried out using methods known in the art (e.g. by chromatography on chiral phases, etc.) If the compounds 2 are used in the form of their enantiomers, it is particularly preferable to use the enantiomers in the R configuration at the C—OH group.

Optionally, the inhalation device according to the invention contains plural of doses of a medicament in powder form that contains beside one compound of formula 1a steroid 3 as another active ingredient.

In such medicament combinations the steroid 3 is preferably selected from among prednisolone, prednisone, butixocortpropionate, RPR-106541, flunisolide, beclomethasone, triamcinolone, budesonide, fluticasone, mometasone, ciclesonide, rofleponide, ST-126, dexamethasone, (S)-fluoromethyl 6α,9α-difluoro-17α-[(2-furanylcarbonyl)oxy]-11[beta]-hydroxy-16α-methyl-3-oxo-androsta-1,4-diene-17β-carbothionate, (S)-(2-oxo-tetrahydro-furan-3S-yl)6α,9α-difluoro-1 1 β-hydroxy-16α-methyl-3-oxo-17α-propionyloxy-androsta-1,4-diene-17β-carbothionate, and etiprednoldichloroacetate (BNP-166), optionally in the form of the racemates, enantiomers or diastereomers thereof and optionally in the form of the salts and derivatives thereof, the solvates and/or hydrates thereof.

In particularly preferred medicament combinations the steroid 3 is selected from the group comprising flunisolide, beclomethasone, triamcinolone, budesonide, fluticasone, mometasone, ciclesonide, rofleponide, ST-126, dexamethasone, (S)-fluoromethyl 6α,9α-difluoro-1 Ia-[(2-furanylcarbonyl)oxy]-11β-hydroxy-16α-methyl-3-oxo-androsta-1,4-diene-17β-carbothionate, (S)-(2-oxo-tetrahydro-furan-3S- yl)6α,9α-difluoro-11β-hydroxy-16α-methyl-3-oxo-17α-propionyloxy-androsta-1,4-diene-17β-carbothionate, and etiprednol-dichloroacetate, optionally in the form of the racemates, enantiomers or diastereomers thereof and optionally in the form of the salts and derivatives thereof, the solvates and/or hydrates thereof.

In particularly preferred medicament combinations the steroid 3 is selected from the group comprising budesonide, fluticasone, mometasone, ciclesonide, (S)-fluoromethyl 6α,9α-difluoro-1 Ia-[(2-furanylcarbonyl)oxy]-11β-hydroxy-16α-methyl-3-oxo-androsta-1, A-diene-17β-carbothionate, and etiprednol-dichloroacetate, optionally in the form of the racemates, enantiomers or diastereomers thereof and optionally in the form of the salts and derivatives thereof, the solvates and/or hydrates thereof.

Any reference to steroids 3 includes a reference to any salts or derivatives, hydrates or solvates thereof which may exist. Examples of possible salts and derivatives of the steroids 3 may be: alkali metal salts, such as for example sodium or potassium salts, sulphobenzoates, phosphates, isonicotinates, acetates, propionates, dihydrogen phosphates, palmitates, pivalates or furcates.

Optionally, the inhalation device according to the invention contains plural of doses of a medicament on powder form that contains beside one compound of formula 1 additionally both, one of the betamimetics 2 mentioned hereinbefore and one of the steroids 3 mentioned hereinbefore.

According to one aspect, there is provided an inhalation device according to the invention, wherein each blister contains a pharmaceutical composition in powder form wherein the pharmaceutical composition comprises one or more, preferably one, compound of formula 1.

Within the scope of the inhalable powders according to the invention the excipients have a maximum average particle size of up to 250 μm, preferably between 10 and 150 μm, most preferably between 15 and 80 μm. It may sometimes seem appropriate to add finer excipient fractions with an average particle size of 1 to 9 μm to the excipients mentioned above. These finer excipients are also selected from the group of possible excipients listed hereinbefore. Finally, in order to prepare the inhalable powders according to the invention, micronised active substance I—, and optionally 2 and/or 3, preferably with an average particle size of 0.5 to 10 μm, more preferably from 1 to 6 μm, is added to the excipient mixture. Processes for producing the inhalable powders according to the invention by grinding and micronising and finally mixing the ingredients together are known from the prior art.

For the methods of preparing the pharmaceutical compositions in powder form reference may be made to the disclosure of WO 02/30390, WO 03/017970, or WO 03/017979 for example. The disclosure of WO 02/30390, WO 03/017970, and WO 03/017979 is hereby incorporated by reference into the instant patent application in its entirety.

As an example, the pharmaceutical compositions according to the invention may be obtained by the method described below.

First, the excipient and the active substance are placed in a suitable mixing container. The active substance used has an average particle size of 0.5 to 10 μm, preferably 1 to 6 μm, most preferably 2 to 5 μm. The excipient and the active substance are preferably added using a sieve or a granulating sieve with a mesh size of 0.1 to 2 mm, preferably 0.3 to 1 mm, most preferably 0.3 to 0.6 mm. Preferably, the excipient is put in first and then the active substance is added to the mixing container. During this mixing process the two components are preferably added in batches. It is particularly preferred to sieve in the two components in alternate layers. The mixing of the excipient with the active substance may take place while the two components are still being added. Preferably, however, mixing is only done once the two components have been sieved in layer by layer.

If after being chemically prepared the active substance used in the process described above is not already obtainable in a crystalline form with the particle sizes mentioned earlier, it can be ground up into the particle sizes which conform to the abovementioned parameters (so-called micronising).

The invention claimed is:

1. An inhaler comprising a housing, a blister strip contained within said housing, said blister strip having a surface and a plurality of blister pockets depending from said surface, each blister pocket containing a dose of medicament for inhalation by a user and, a blister strip drive mechanism including a drive wheel comprising a plurality of spokes, each spoke forming an arm of the blister drive mechanism, and a blister strip drive member shaped to contact the strip along a line defined by a crease between a blister pocket and said surface, to drive said strip, the blister strip drive member having leading and trailing blister strip contact edges on opposite sides of an axis extending in a radial direction through said arm and the blister strip drive member so that the leading blister strip contact edge contacts the strip along a line defined by the crease between one blister pocket and said surface when the drive member is rotated in one direction and so that the trailing blister strip contact edge contacts the strip along a line defined by the crease between an adjacent blister pocket and said surface, when the drive member is rotated in the opposite direction, wherein a blister separation, which is the distance between the creases of adjacent blister pockets, is substantially the same as the distance between the leading and trailing edges of the blister strip drive member and wherein the pitch of the blister strip is selected so that it is less than the pitch of the drive wheel, with the pitch of the blister strip being equal to the width of the blister plus the blister separation and the pitch of the blister strip drive member being equal to the length of a chord of the blister strip drive member plus the width of a tip of the blister strip drive member.

2. An inhaler according to claim 1, wherein the blister strip drive member is configured to direct a larger component of force in a direction along the surface of the strip relative to a component of force directed against a blister pocket.

3. An inhaler according to claim 1, wherein the blister strip drive member is disposed on an end of said arm.

4. An inhaler according to claim 1, wherein the blister strip contact edge has a radius of up to 0.2 mm.

5. An inhaler according to claim 1, wherein the blister strip drive member comprises an enlarged head on the end of the arm that tapers from the arm to the blister strip contact edge.

6. An inhaler according to claim 1, wherein the blister strip drive member and arm are configured so that contact with the blister strip is restricted to the blister strip contact edge.

7. An inhaler according to claim 1, wherein the arm, the blister strip drive member, or both are shaped such that the blister strip contact edge contacts the crease between a shaped blister pocket and the surface of the strip.

8. An inhaler according to claim 1, wherein the arm, the blister strip drive member, or both are at least partially curved in shaped such that the blister strip contact edge contacts at least a partially curved line defined by the crease between a shaped blister pocket and the surface of the strip.

9. An inhaler according to claim 1, wherein an end view of the blister strip drive member is substantially triangular or part triangular in shape, the apex of the triangle pointing in a radially inward direction along the length of the arm.

10. An inhaler according to claim 1, wherein the blister strip drive member has a substantially flat or concave end face extending between said blister strip contact edges.

11. An inhaler according to claim 1, wherein said end face extends in a plane lying substantially at right angles to a plane of the arm.

12. An inhaler according to claim 1, wherein the drive mechanism is configured to sequentially move a blister into alignment with a blister opening member.

13. An inhaler according to claim 12, wherein the inhaler comprises a mouthpiece and a cap to cover the mouthpiece, the drive mechanism being operable in response to movement of the cap by a user.

14. An inhaler according to claim 1, wherein each blister pocket has a part cylindrical central region and part hemispherical end regions.

* * * * *